(12) United States Patent
Wang et al.

(10) Patent No.: US 9,920,022 B2
(45) Date of Patent: Mar. 20, 2018

(54) SMALL MOLECULE COMPOUND AND SYNTHESIZING METHOD AND USES THEREOF

(71) Applicant: TECHNODERMA MEDICINES PTE LTD., Jiaxing (CN)

(72) Inventors: Zengquan Wang, Shanghai (CN); Sheldon Cao, Shanghai (CN); Chen Mao, Shanghai (CN)

(73) Assignee: TECHNODERMA MEDICINES PTE LTD., Jiaxing (CN)

( * ) Notice: Subject to any disclaimer, the term of this patent is extended or adjusted under 35 U.S.C. 154(b) by 0 days.

(21) Appl. No.: 15/431,779

(22) Filed: Feb. 14, 2017

(65) Prior Publication Data

US 2017/0158651 A1   Jun. 8, 2017

Related U.S. Application Data

(63) Continuation of application No. PCT/CN2015/086908, filed on Aug. 13, 2015.

(30) Foreign Application Priority Data

Aug. 14, 2014  (CN) .......................... 2014 1 0398184

(51) Int. Cl.

| | |
|---|---|
| *C07D 295/096* | (2006.01) |
| *C07D 211/14* | (2006.01) |
| *C07D 211/46* | (2006.01) |
| *C07D 211/52* | (2006.01) |
| *C07D 209/04* | (2006.01) |
| *C07D 241/08* | (2006.01) |
| *C07C 315/04* | (2006.01) |
| *C07C 317/22* | (2006.01) |
| *C07C 259/06* | (2006.01) |
| *A61K 8/42* | (2006.01) |
| *A61Q 7/00* | (2006.01) |
| *C07D 209/44* | (2006.01) |
| *C07D 217/04* | (2006.01) |

(52) U.S. Cl.
CPC ............ *C07D 295/096* (2013.01); *A61K 8/42* (2013.01); *A61Q 7/00* (2013.01); *C07C 259/06* (2013.01); *C07C 315/04* (2013.01); *C07C 317/22* (2013.01); *C07D 209/44* (2013.01); *C07D 211/14* (2013.01); *C07D 211/46* (2013.01); *C07D 211/52* (2013.01); *C07D 217/04* (2013.01); *C07D 241/08* (2013.01)

(58) Field of Classification Search
CPC .. C07D 295/06; C07D 211/46; C07D 211/52; C07D 211/14; C07D 209/04; C07D 241/08; C07C 259/06; C07C 315/04; A61Q 7/00
USPC ............... 564/300; 544/106, 350; 514/231.2, 514/252.12, 317, 408, 412
See application file for complete search history.

(56) References Cited

U.S. PATENT DOCUMENTS

2017/0158651 A1* 6/2017 Wang .................. C07D 295/096

FOREIGN PATENT DOCUMENTS

| | | |
|---|---|---|
| CA | 2403806 A1 | 9/2002 |
| CN | 103479627 A | 1/2014 |
| CN | 104193699 A | 12/2014 |
| WO | 200170687 A1 | 9/2001 |

OTHER PUBLICATIONS

PCT/CN2016/076333 International Search Report (dated Oct. 10, 2016) (In Chinese).

* cited by examiner

*Primary Examiner* — Venkataraman Balasubramanian
(74) *Attorney, Agent, or Firm* — Wayne & King LLC

(57) ABSTRACT

Provided is a small molecule compound as represented by structural formula (I). The product of the present invention in various concentrations and dosages can achieve an obvious change in the growth period of hairs, promoting the growth of the hairs, thus exhibiting an obvious effect of promoting hair growth. In addition, changes in the weight of a mouse in each group are slow, indicating that the test compound does not cause weight loss in an animal.

11 Claims, 23 Drawing Sheets

SMALL MOLECULE COMPOUND AND SYNTHESIZING METHOD AND USES THEREOF

CROSS-REFERENCE TO RELATED APPLICATIONS

This application is a continuation of International Patent Application No. PCT/CN2015/086908 with a filing date of Aug. 13, 2015, designating the United States, now pending, and further claims priority to Chinese Patent Application No. 201410398184.1 with a filing date of Aug. 14, 2014. The content of the aforementioned application, including any intervening amendments thereto, are incorporated herein by reference.

TECHNICAL FIELD

The present invention relates to the field of chemical synthesis, in particular to a small molecule compound and method of synthesizing the compound and uses thereof.

BACKGROUND OF THE INVENTION

Hair follicle (HF) is a miniorgan that repeats the course of perpetual cycles through three distinct phases, anagen (growth phase), catagen (regressing phase) and telogen (resting phase). During anagen, hair bulb keratinocytes (HBKs) proliferate and differentiate vigorously, leading to the growth extension of the hair shaft.

At present, it is reported that many biological factors play a role in regulation and synchronization of HF cycle. Those factors can be divided to different categories, such as hormone, growth factor, enzyme and transcription factors. Specifically, for example, studies using gene knockout or transgenic mice have indicated that sonic hedgehog and keratinocyte growth factor initiate the onset of anagen, while transforming growth factor-β, fibroblast growth factor-5 and nerve growth factor accelerate the transition from anagen to catagen by inducing HBK apoptosis. The HF cycle can be controlled finely by these factors under normal conditions.

However, studies indicate that, a variety of pathological stimuli induced by stress or excess androgen cause a disorder in HF cycle, including shortening of anagen duration and prolongation of telogen duration, resulting in hair shedding and so on.

To date, there are a few targeted drugs available in the market, especially two drugs approved by FDA: Minoxidil and Finasteride. Minoxidil is originally developed for hypertension. During treatment, it was found that almost all patients administered with Minoxidil showed symptoms of hirsutism. In 1996, 2% Minoxidil solution was approved as OTC drug for treating alopecia caused by androgen. Finasteride is currently the only drug approved by FDA for androgenetic alopecia in clinics, it is a 5 alpha-reductase inhibitor and can inhibit activity of 5 alpha-reductase (type II), so that conversion of testosterone into dihydrotestosterone (DHT) in hair is blocked, thus the level of DHT in hair baldness area is reduced (promoting hair growth).

Nevertheless, with the development of times, disorders associated with hair are prevalent. Therefore, there is a pressing need for further study in diversity and multiplicity of related drugs for disorders associated with hair.

SUMMARY OF THE INVENTION

The present invention is aimed to develop a new drug that can be used for promoting hair growth.

A small molecule compound, characterized that it is represented by the following structural formula:

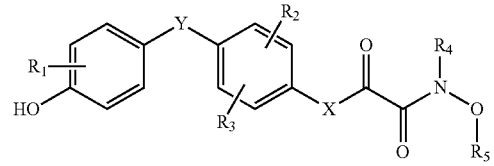

$R_1$ is selected from hydrogen, halogen, $C_0$-$C_6$ alkyl or optionally substituted with 1-3 substituents, cyano, isocyanate, amide, iso-sulfonamide (—$SO_2NHR$), iso-sulfinyl (SONH), sulfonamide (NHSO$_2$R), sulfonamido (NHSOR), S-alkyl, S-aryl, S-heteroaryl (SHet);

wherein the substituents are selected from halogen, aryl, substituted aryl, heteroaryl, O-alkyl, O-aryl, O-heteroaryl, N-alkyl, N-aryl, N-heteroaryl;

$R_2$ is selected from hydrogen, halogen, $C_0$-$C_6$ alkyl or substituted alkyl, alkoxy, aryl, substituted aryl, benzyl, substituted benzyl;

$R_3$ is selected from hydrogen, halogen, $C_0$-$C_6$ alkyl or substituted alkyl, alkoxy, aryl, substituted aryl, benzyl, substituted benzyl;

$R_4$ is selected from hydrogen, $C_1$-$C_6$ alkyl or substituted alkyl;

$R_5$ is selected from hydrogen, $C_0$-$C_6$ alkyl or substituted alkyl;

X is selected from alkyl or substituted alkyl, amino or substituted amino;

Y is selected from alkyl or substituted alkyl, oxygen, sulfur, amino, carbonyl, sulfoxide, sulfone.

In the above mentioned optional groups of $R_1$-$R_5$, the concerned alkyls can be substituted or un-substituted linear alkyl, branched alkyl, cycloalkyl; when it is cycloalkyl, carbon atom on the ring of alkyl can be substituted with any of O, S and N, and any one or more bonds in ring structure can link aromatic groups or heteroaromatic groups;

The small molecule compound provided in the present invention can preferably represented by the following structural formula:

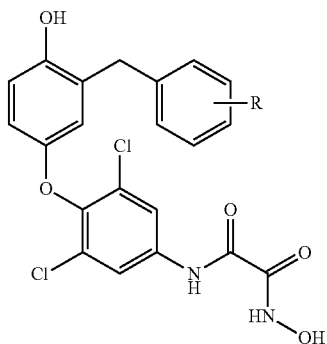

wherein R is mono- or polysubstituted halogen, alkylsulphonyl, alkyl, methoxy, nitro, amino, carboxyl, ester, hydroxyl, aryl, benzyl, hydrogen.

The small molecule compound provided in the present invention can preferably represented by the following structural formula:

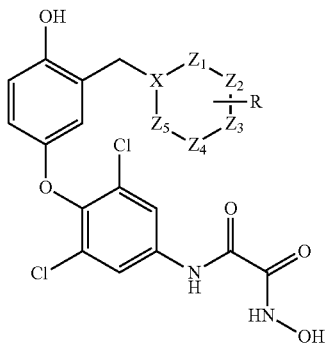

wherein R is mono- or polysubstituted halogen, alkylsulphonyl, alkyl, methoxy, nitro, amino, carboxyl, ester, hydroxyl, aryl, benzyl, hydrogen, O-alkyl, O-aryl, O-heteroaryl, N-alkyl, N-aryl. N-heteroaryl;

X is carbon or nitrogen;

$Z_1$, $Z_2$, $Z_3$, $Z_4$, $Z_5$ is carbon, oxygen, sulfur, nitrogen, carbonyl (i.e., to form aromatic or nonaromatic lactam).

The small molecule compound provided in the present invention can also preferably represented by the following structural formula:

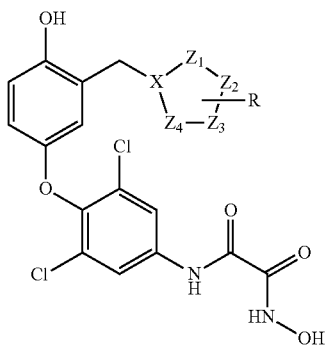

wherein R is mono- or polysubstituted halogen, alkylsulphonyl, alkyl, methoxy, nitro, amino, carboxyl, ester, hydroxyl, aryl, benzyl, hydrogen, O-alkyl, O-aryl, O-heteroaryl, N-alkyl, N-aryl. N-heteroaryl;

X is carbon or nitrogen;

$Z_1$, $Z_2$, $Z_3$, $Z_4$ can be carbon, oxygen, sulfur, nitrogen, carbonyl (i.e., to form aromatic or nonaromatic lactam).

In the three preferred structures described above, in optional group of R, the concerned alkyl can be substituted or un-substituted linear alkyl, branched alkyl, cycloalkyl; when it is polysubstituted, it can form covalent bond with $Z_1$-$Z_5$, or it can also form an aromatic, hetero-aromatic or cyclic alkyl linked with any one or any several bonds of $Z_1$ and $Z_2$, $Z_2$ and $Z_3$, $Z_3$ and $Z_4$, $Z_4$ and $Z_5$, respectively.

The small molecule provided in this invention can preferably be:

N1-(3,5-dichloro-4-(3-(4-fluorobenzyl)-4-hydroxyphenoxy)phenyl)-N2-oxalyl hydroxylamine (hydroxyoxalamide), its structural formula is:

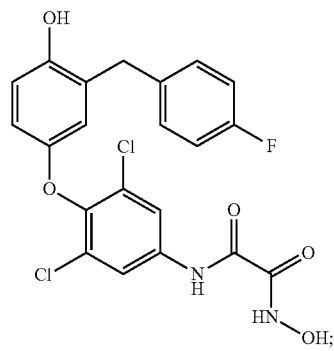 [SMILES: O=C(NO)C(=O)Nc1cc(Cl)c(Oc2ccc(O)c(Cc3ccc(F)cc3)c2)c(Cl)c1]

N1-(3,5-dichloro-4-(3-(4-methylsulfonylbenzyl)-4-hydroxyphenoxy)phenyl)-N2-oxalyl hydroxylamine, its structural formula is:

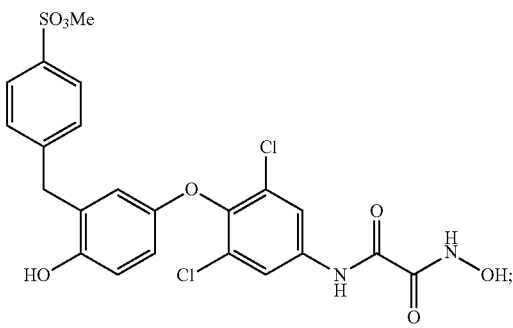

N1-(3,5-dichloro-4-(3-(4-methylbenzyl)-4-hydroxyphenoxy)phenyl)-N2-oxalyl hydroxylamine, its structural formula is:

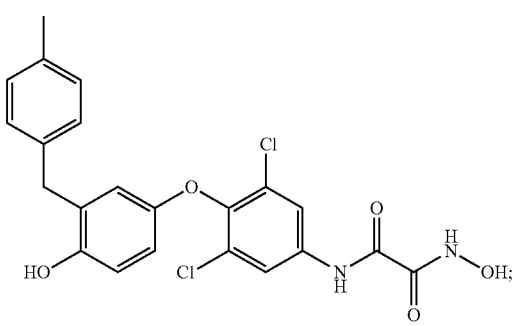 [SMILES: Cc1ccc(Cc2cc(Oc3c(Cl)cc(NC(=O)C(=O)NO)cc3Cl)ccc2O)cc1]

N1-(3,5-dichloro-4-(3-(3,4-dichlorobenzyl)-4-hydroxyphenoxy)phenyl)-N2-oxalyl hydroxylamine, its structural formula is:

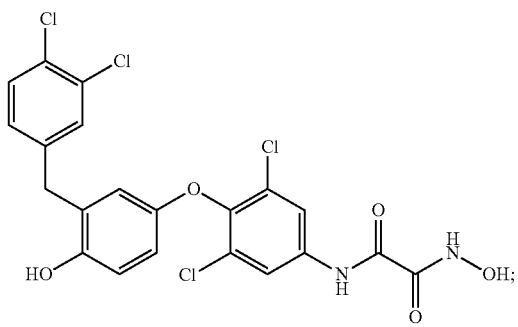 [SMILES: O=C(NO)C(=O)Nc1cc(Cl)c(Oc2ccc(O)c(Cc3ccc(Cl)c(Cl)c3)c2)c(Cl)c1]

N1-(3,5-dichloro-4-(3-(3-fluorobenzyl)-4-hydroxyphenoxy)phenyl)-N2-oxalyl hydroxylamine, its structural formula is:

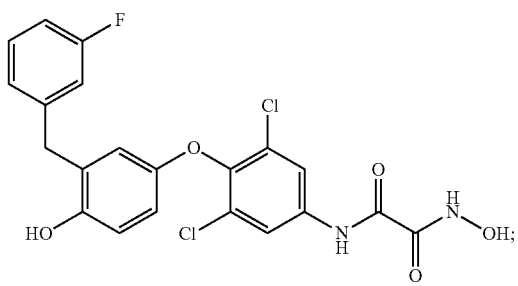 [SMILES: O=C(NO)C(=O)Nc1cc(Cl)c(Oc2ccc(O)c(Cc3cccc(F)c3)c2)c(Cl)c1]

N1-(3,5-dichloro-4-(3-(2-fluorobenzyl)-4-hydroxyphenoxy)phenyl)-N2-oxalyl hydroxylamine, its structural formula is:

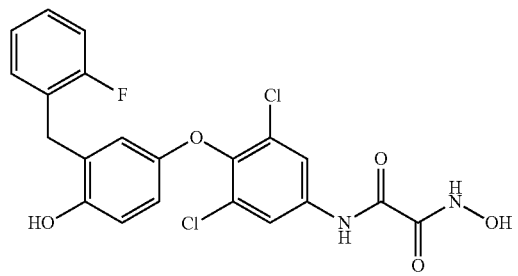 [SMILES: O=C(NO)C(=O)Nc1cc(Cl)c(Oc2ccc(O)c(Cc3ccccc3F)c2)c(Cl)c1]

N1-(3,5-dichloro-4-(4-hydroxy-3-(morpholinomethyl)phenoxy)phenyl)-N2-oxalyl hydroxylamine, its structural formula is:

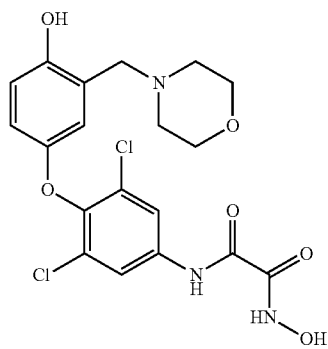 [SMILES: O=C(NO)C(=O)Nc1cc(Cl)c(Oc2ccc(O)c(CN3CCOCC3)c2)c(Cl)c1]

N1-(3,5-dichloro-4-(4-hydroxy-3-(4-hydroxypiperidin-1-yl)phenoxy)phenyl)-N2-oxalyl hydroxylamine, its structural formula is:

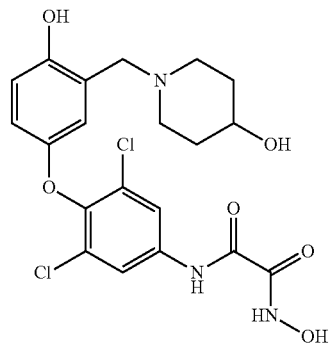 [SMILES: O=C(NO)C(=O)Nc1cc(Cl)c(Oc2ccc(O)c(CN3CCC(O)CC3)c2)c(Cl)c1]

N1-(3,5-dichloro-4-(4-hydroxy-3-(4-methylpiperazin-1-methyl)phenoxy)phenyl)-N2-oxalyl hydroxylamine, its structural formula is:

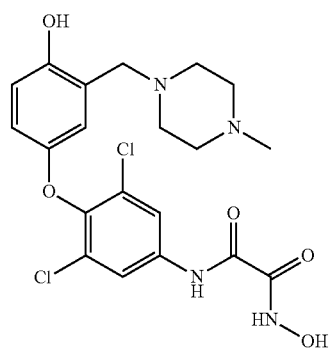 [SMILES: CN1CCN(Cc2cc(Oc3c(Cl)cc(NC(=O)C(=O)NO)cc3Cl)ccc2O)CC1]

N1-(3,5-dichloro-4-(4-hydroxy-3-(pyrrolidin-1-methyl)phenoxy)phenyl)-N2-oxalyl hydroxylamine, its structural formula is:

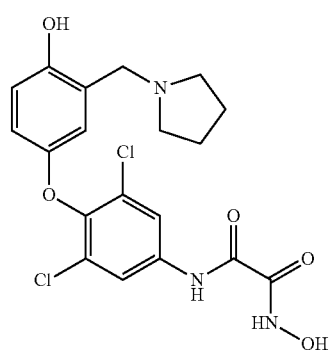 [SMILES: O=C(NO)C(=O)Nc1cc(Cl)c(Oc2ccc(O)c(CN3CCCC3)c2)c(Cl)c1]

N1-(4-(3-((4-benzylpiperidin-1-methyl)-4-hydroxyphenoxy)-3,5-dichlorophenyl)-N2-oxalyl hydroxylamine, its structural formula is:

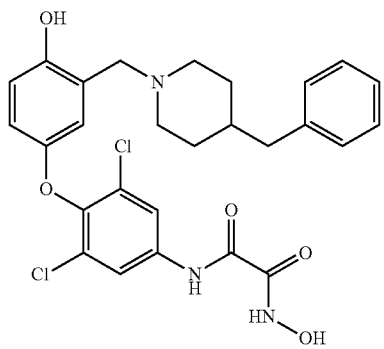 [SMILES: O=C(NO)C(=O)Nc1cc(Cl)c(Oc2ccc(O)c(CN3CCC(Cc4ccccc4)CC3)c2)c(Cl)c1]

N1-(3,5-dichloro-4-(4-hydroxy-3-((4-hydroxy-4-phenylpiperidin-1-methyl)phenoxy)phenyl)-N2-oxalyl hydroxylamine, its structural formula is:

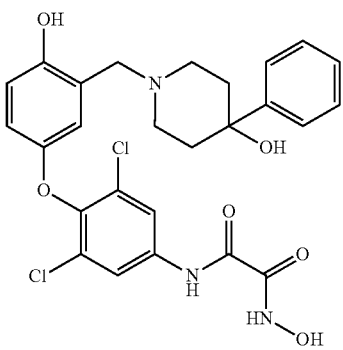 [SMILES: O=C(NO)C(=O)Nc1cc(Cl)c(Oc2ccc(O)c(CN3CCC(O)(c4ccccc4)CC3)c2)c(Cl)c1]

N1-(3,5-dichloro-4-(4-hydroxy-3-(isoindolin-2-methyl)phenoxy)phenyl)-N2-oxalyl hydroxylamine, its structural formula is:

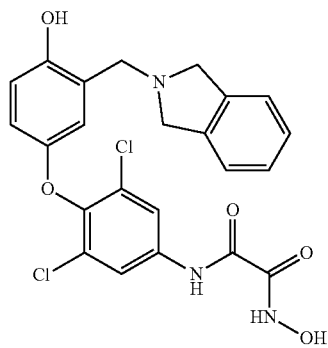 [SMILES: O=C(NO)C(=O)Nc1cc(Cl)c(Oc2ccc(O)c(CN3Cc4ccccc4C3)c2)c(Cl)c1]

N1-(3,5-dichloro-4-(3-(3,4-dihydroisoquinolin-2(1H)-methyl)-4-hydroxyphenoxy)phenyl)-N2-oxalyl hydroxylamine, its structural formula is:

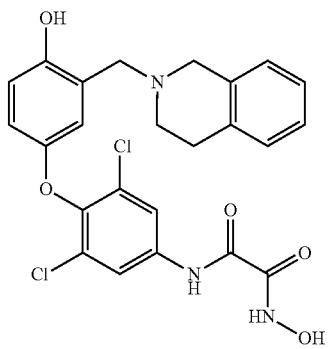 [SMILES: O=C(NO)C(=O)Nc1cc(Cl)c(Oc2ccc(O)c(CN3CCc4ccccc4C3)c2)c(Cl)c1]

N1-(3,5-dichloro-4-(4-hydroxy-3-(3-piperazinone-1-methyl)phenoxy)phenyl)-N2-oxalyl hydroxylamine, its structural formula is:

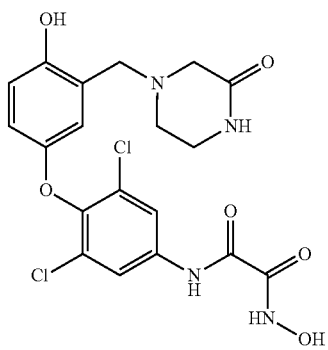 [SMILES: O=C1CN(Cc2cc(Oc3c(Cl)cc(NC(=O)C(=O)NO)cc3Cl)ccc2O)CCN1]

The present invention also provides a method for synthesizing the above small molecule compound, characterized in that: 4-methoxyphenol and 1,2,3-trichloro-5-nitrobenzene are used as starting material.

The specific synthesizing steps are described below:

Step 1: 4-methoxyphenol is reacted with 1,2,3-trichloro-5-nitrobenzene to form 1,3-dichloro-2-(4-methoxyphenoxy)-5-nitrobenzene;

Step 2: 1,3-dichloro-2-(4-methoxyphenoxy)-5-nitrobenzene is reacted with benzoic acid derivatives to form (5-(2,6-dichloro-4-nitrophenoxy)-2-methoxyphenyl)(substituted phenyl) methyl ketone (methanone);

Step 3: 3,5-dichloro-4-(3-(substituted benzyl)-4-methoxyphenoxy)-aniline is obtained from reduction of carbonyl and nitro of (5-(2,6-dichloro-4-nitrophenoxy)-2-methoxyphenyl)(substituted phenyl) methyl ketone to amino;

Step 4: 3,5-dichloro-4-(3-(substituted benzyl)-4-methoxyphenoxy)-aniline is reacted with ethyl oxaloyl monochloride to form 2-((3,5-dichloro-4-(3-(substituted benzyl)-4-methoxyphenoxy) phenyl)amino)-oxoacetate (ethyl oxalyl);

Step 5: 2-((3,5-dichloro-4-(3-(substituted benzyl)-4-methoxyphenoxy) phenyl)amino)-oxoacetate (ethyl oxalyl) is reacted with hydroxylamine hydrochloride to form N1-(3,5-dichloro-4-(3-(substituted benzyl)-4-methoxyphenoxy)phenyl)-N2-oxalyl hydroxylamine;

Step 6: after demethylation of methoxyl of N1-(3,5-dichloro-4-(3-(substituted benzyl)-4-methoxyphenoxy) phenyl)-N2-oxalyl hydroxylamine, a target small molecule compound can be obtained.

The reaction equation of the above steps of process is as follows:

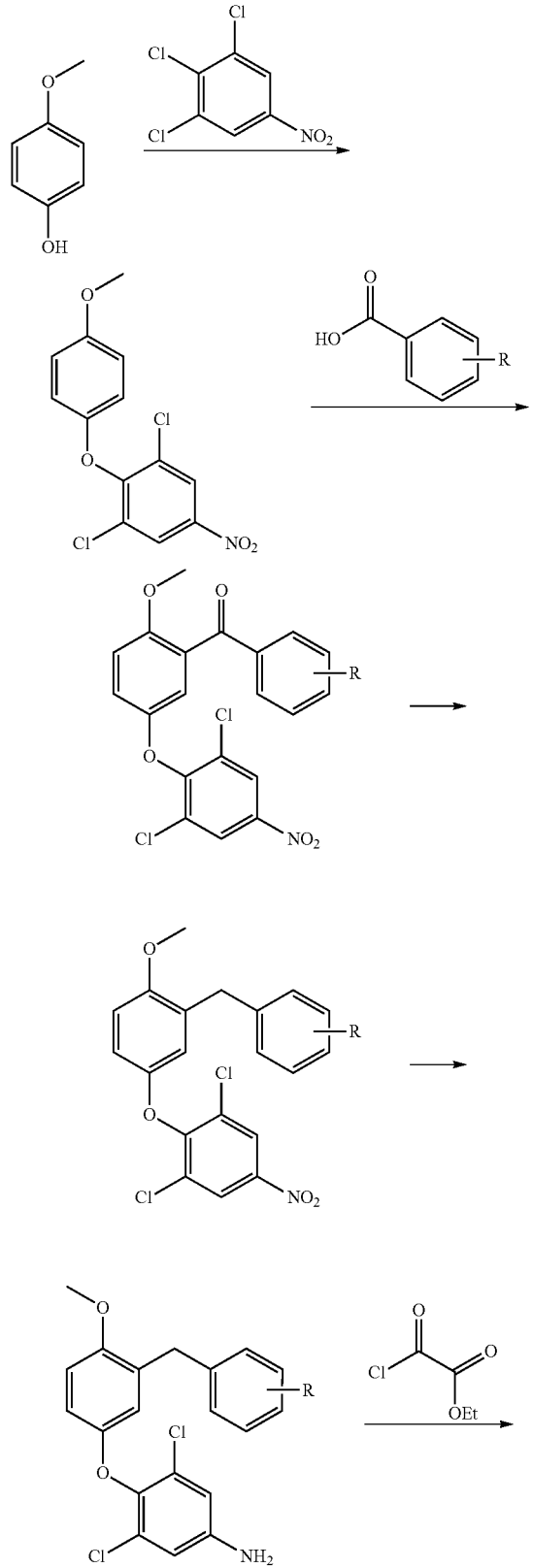

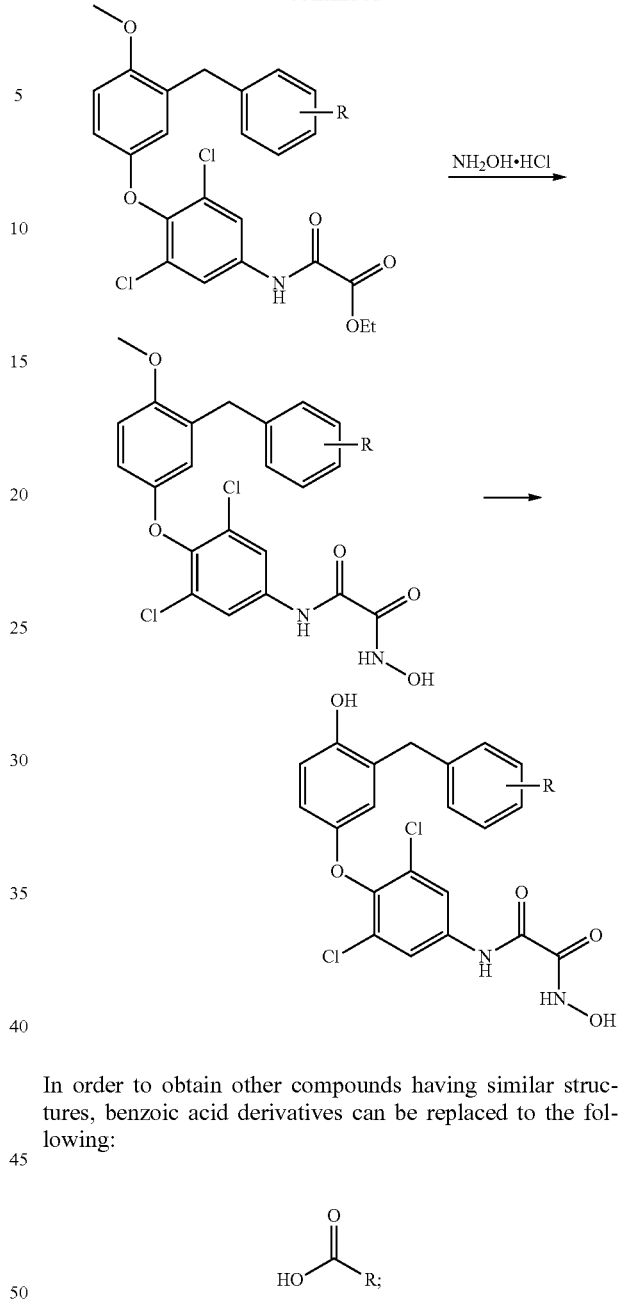

In order to obtain other compounds having similar structures, benzoic acid derivatives can be replaced to the following:

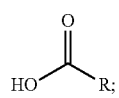

wherein R can be $C_0$-$C_6$ alkyl or optionally substituted with 1-3 substituents;

the substituents are selected from halogen, aryl, substituted aryl, heteroaryl, O-alkyl, O-aryl, O-heteroaryl, N-alkyl, N-aryl, N-heteroaryl, S-alkyl, S-aryl and S-heteroaryl.

Wherein in the step 1, the reaction was carried out under strong basic condition. The molar ratio of strong base to 4-methoxyphenol is 1.5-2:1. The strong bases can be organic or inorganic strong basic reagents that are suitable for forming such ether formation reaction. Preferred is any one from KNH2, NaNH2, NaCN, KCN, butyl lithium, lithium diisopropylamine, benzyl lithium, Grignard reagents, lithium alkylcuprate, sodium methoxide, sodium ethoxide, potassium ethoxide, NaOtBu, NaOH or KOH. The reactions were carried out at 120-160° C. for 1-6 hours.

In addition, the reaction is preferably carried out in DMF and solvent having similar physical/chemical property, the molar ratio of reactants 4-methoxyphenol to 1,2,3-trichloro-5-nitrobenzene is 1:1-2. Preferably, 1,2,3-trichloro-5-nitrobenzene is added (generally 30-60 minutes) after uniform mixing of 4-methoxyphenol and base agent by stirring.

In the step 2, the reaction is carried out in Eaton's Reagent at 80-130° C. for 2 to 8 hours. The molar ratio between 1,3-dichloro-2-(4-methoxyphenoxy)-5-nitrobenzene and benzoic acid derivative is 1:1.25-2.

In the step 3, the purpose is reducing the carbonyl group to methylene group. In the present invention, trifluoroacetic acid and triethyl silane are preferably used to reduce the carbonyl group to methylene group, when using the above reducing agents, the molar ratio of the reactants 5-(2,6-dichloro-4-nitrophenoxy)-2-methoxyphenyl)(substituted phenyl) methyl ketone:trifluoroacetic acid:triethyl silane is 1:4-6:3-5. The preferred solvents are Dichloromethane (DCM), chloroform and tetrachloromethane etc. The reaction is carried out at room temperature for 1-6 hours.

In the step 4, the purpose is reducing nitro group to amino group, in the present invention, the reducing agents can be $SnCl_2$, iron, zinc, platinum, nickel, etc. The molar ratio of 5-(2,6-dichloro-4-nitrophenoxy)-2-methoxyphenyl)(substituted phenyl) methyl ketone to reducing agent is 1:10-20, and the reflux reaction is carried out for 1-6 hours.

In the step 5, the molar ratio of 3,5-dichloro-4-(3-(substituted benzyl)-4-methoxyphenoxy)aniline to ethyl oxalyl monochloride is 1:1.5-3. The molar ratio of ethyl oxalyl monochloride to triethylamine is 1:1.3-2.3. The reaction time is ranged from 0.5-3 hours.

In the step 6, the molar ratio of 2-((3,5-dichloro-4-(3-(substituted benzyl)-4-methoxyphenoxy)phenyl)amino)-oxoacetate (ethyl oxalyl) to hydroxylamine hydrochloride is 1:5-10. The molar ratio between hydroxylamine hydrochloride and base (e.g., NaOH) is 1:1. The reaction time is ranged from 8-14 hours.

In the step 7, the demethylation can be carried out using $AlCl_3$, $ZnCl_2$ or $BBr_3$. For every 50 mg starting material, 1-5 drops (about 1-20 mg) of demethylation agent is used. The reaction time is ranged from 1-5 hours.

For each step of the reaction mentioned above, solvents can be selected from chloroform, Dichloromethane, tetrachloromethane ($CCl_4$), ethyl acetate, methyl acetate, toluene, benzene, chlorobenzene, DMF, dioxane, ethanol, acetone, etc.

It should be indicated that, in the present invention, the compounds and derivatives thereof according to the invention can be prepared through any general synthesizing route. The above specific synthesizing route is only one of the applicable methods.

A small molecule compound provided in the present invention as described above, characterized in that: it can be applied for hair growth, osteoporosis, obesity, etc., more especially for promoting hair re-growth, it can be used in targeted treatment for androgenetic alopecia.

Function and Effect of the Present Invention

The present invention synthesizes a new kind of substance, which can be applied for hair re-growth.

It is found in hair growth study in the topically administrated mouse that, each concentration dose of the product of the present invention can obviously change hair growth cycle and promote hair growth. The product of the invention shows strong effects in promoting hair growth. In addition, body weights of mouse in each group change slowly, which demonstrates that the tested compound cannot induce loss of body weight.

It can be seen from the above results that, the substance shows no toxic side effects, and has obvious effect in promoting hair growth.

BRIEF DESCRIPTION OF THE DRAWINGS

FIG. 1(b), Photograph of mice with hair growth in the TDM-001-2 group;
FIG. 1 (d), Photograph of mice with hair growth in the TDM-001-4 group.

EXAMPLES

Example 1. Product Number: TMI-105795

Name

Figure 1A:
FIG. 1(a), Photograph of mice with hair growth in the TDM-001-1 group.
Figure 1:
FIG. 1 (c), Photograph of mice with hair growth in the TDM-001-3 group.
Figure 1:
Figure 1:
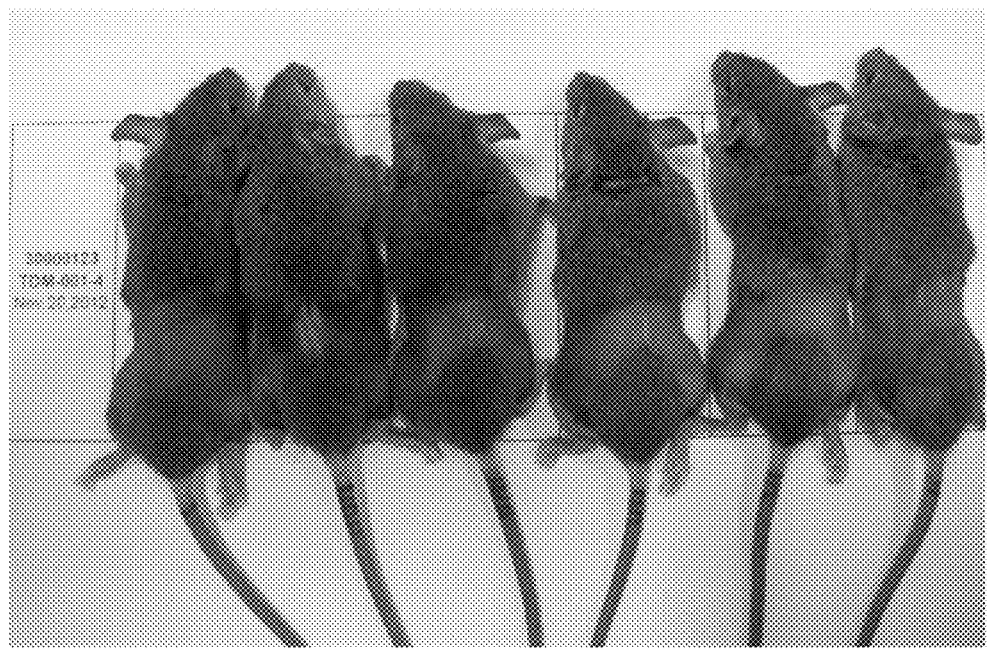
Figure 2:
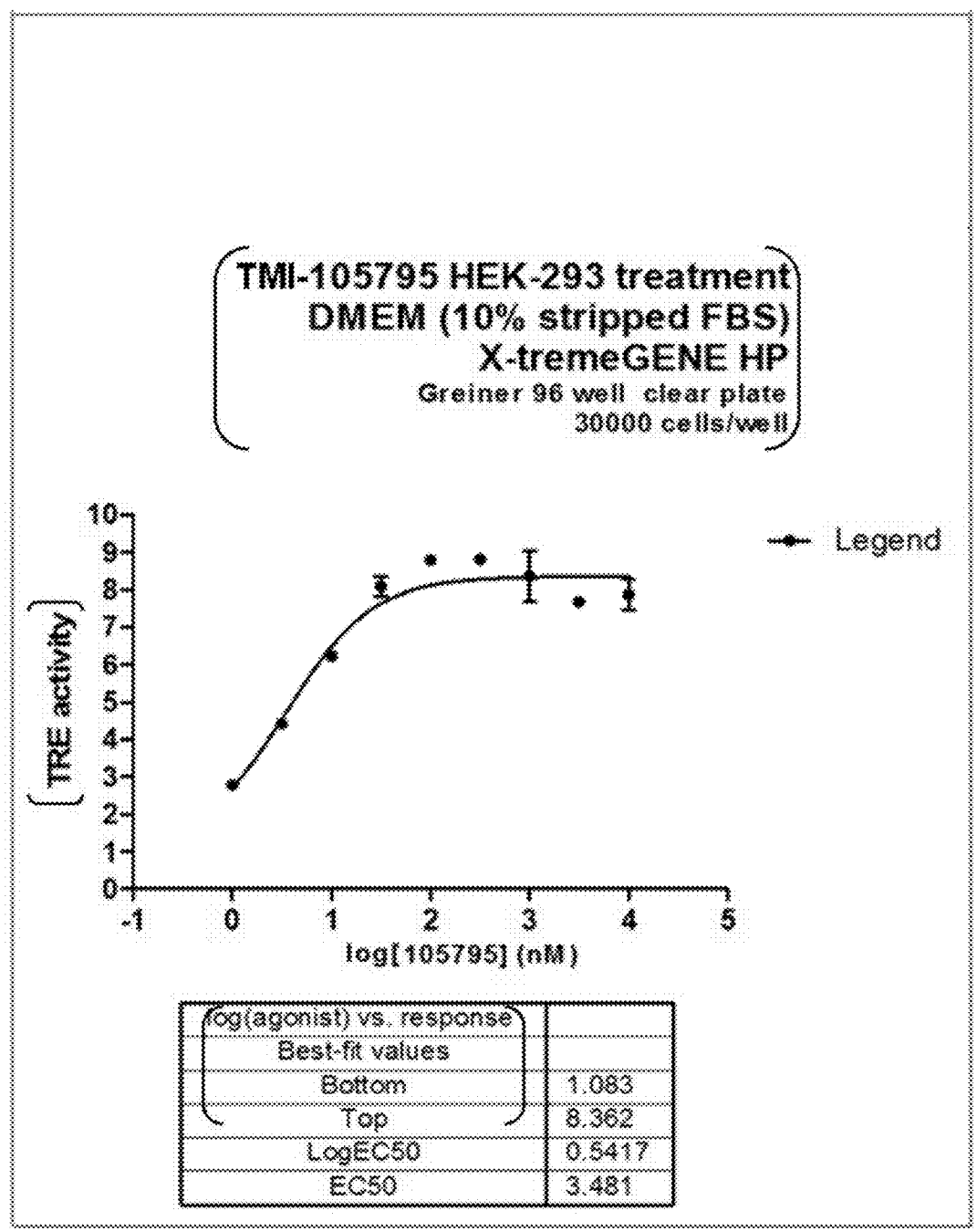
FIG. 2. Experimental results of TMI-105795.
Figure 3:
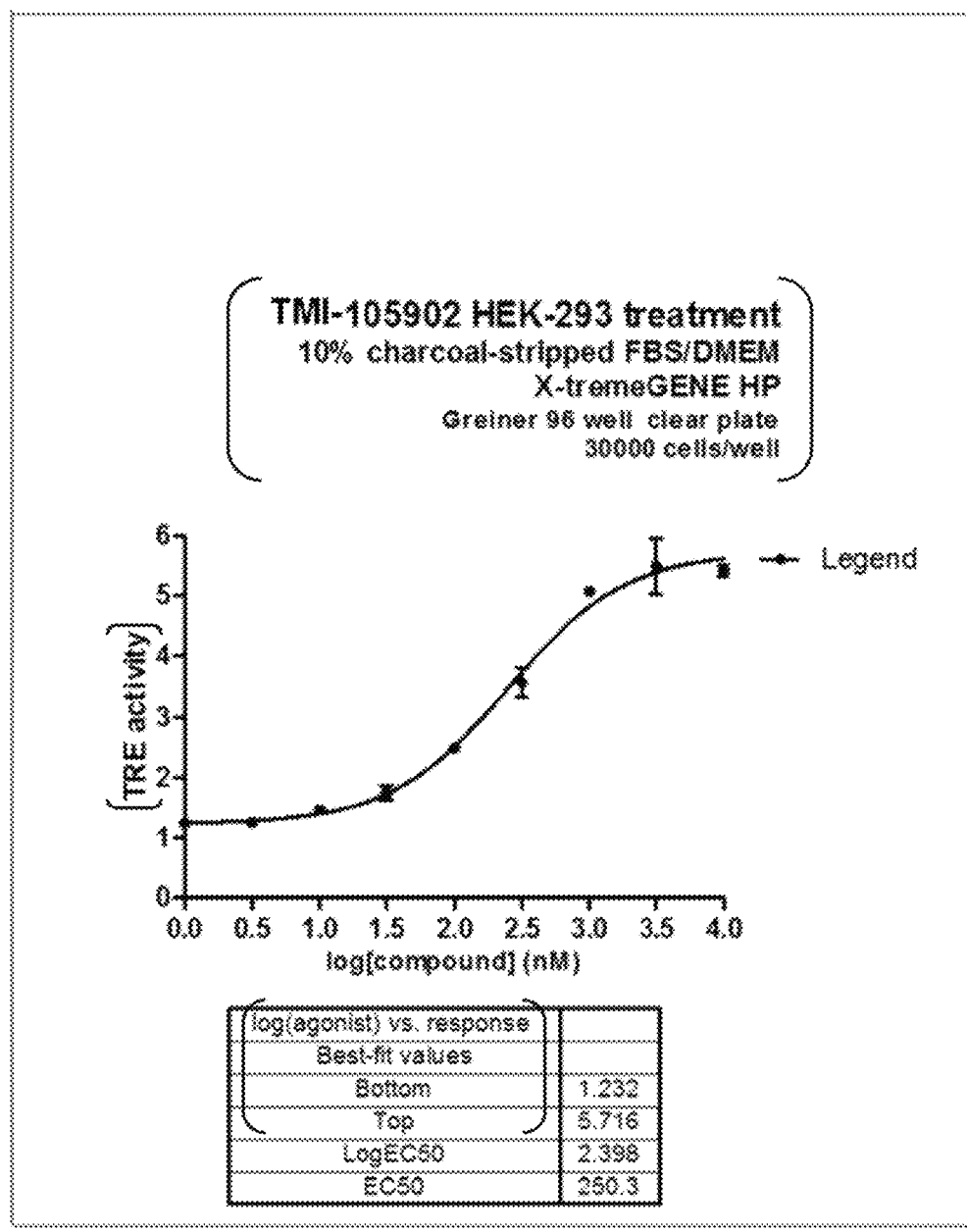
FIG. 3. Experimental results of TMI-105902.
Figure 4:
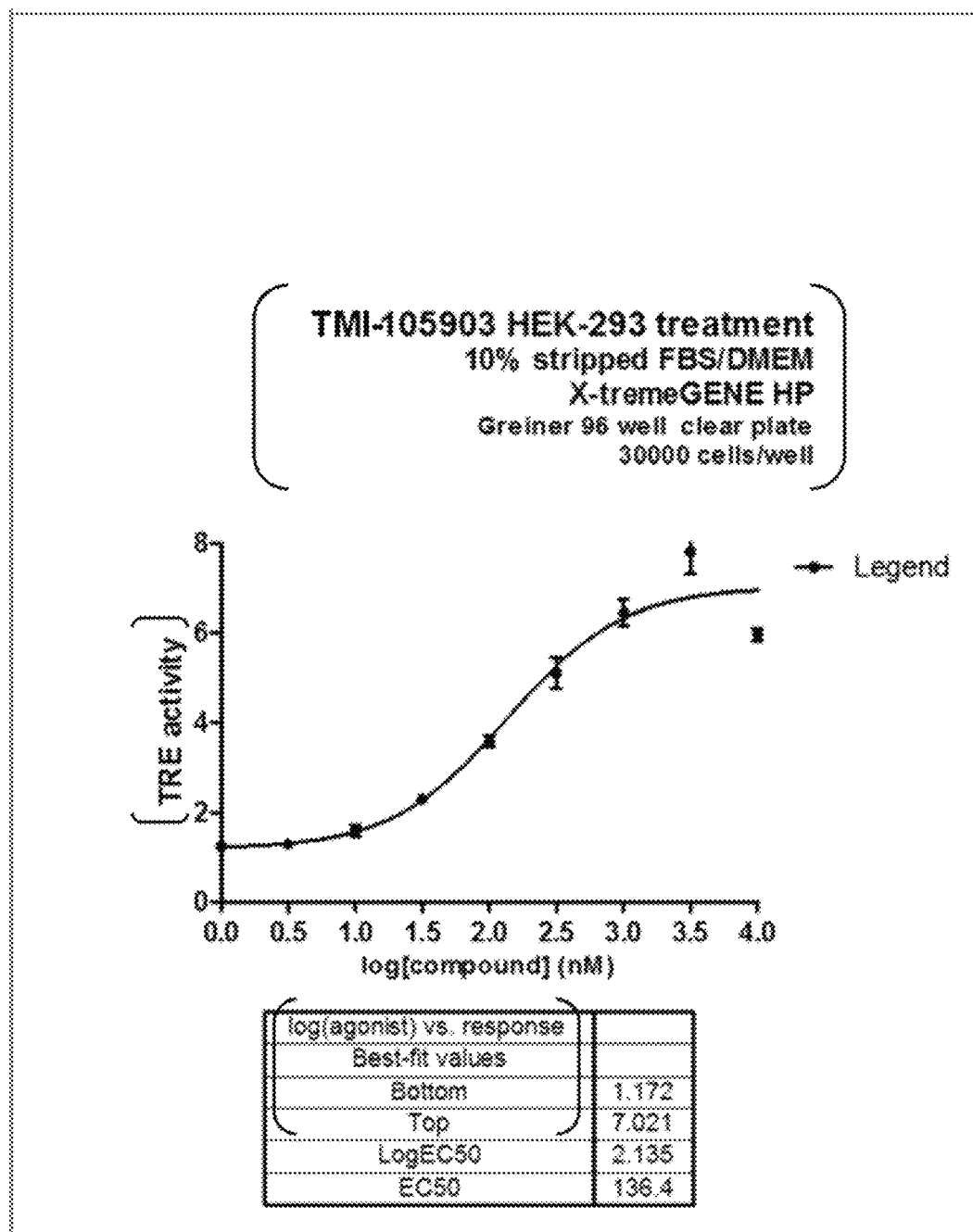
FIG. 4. Experimental results of TMI-105903.
Figure 5:
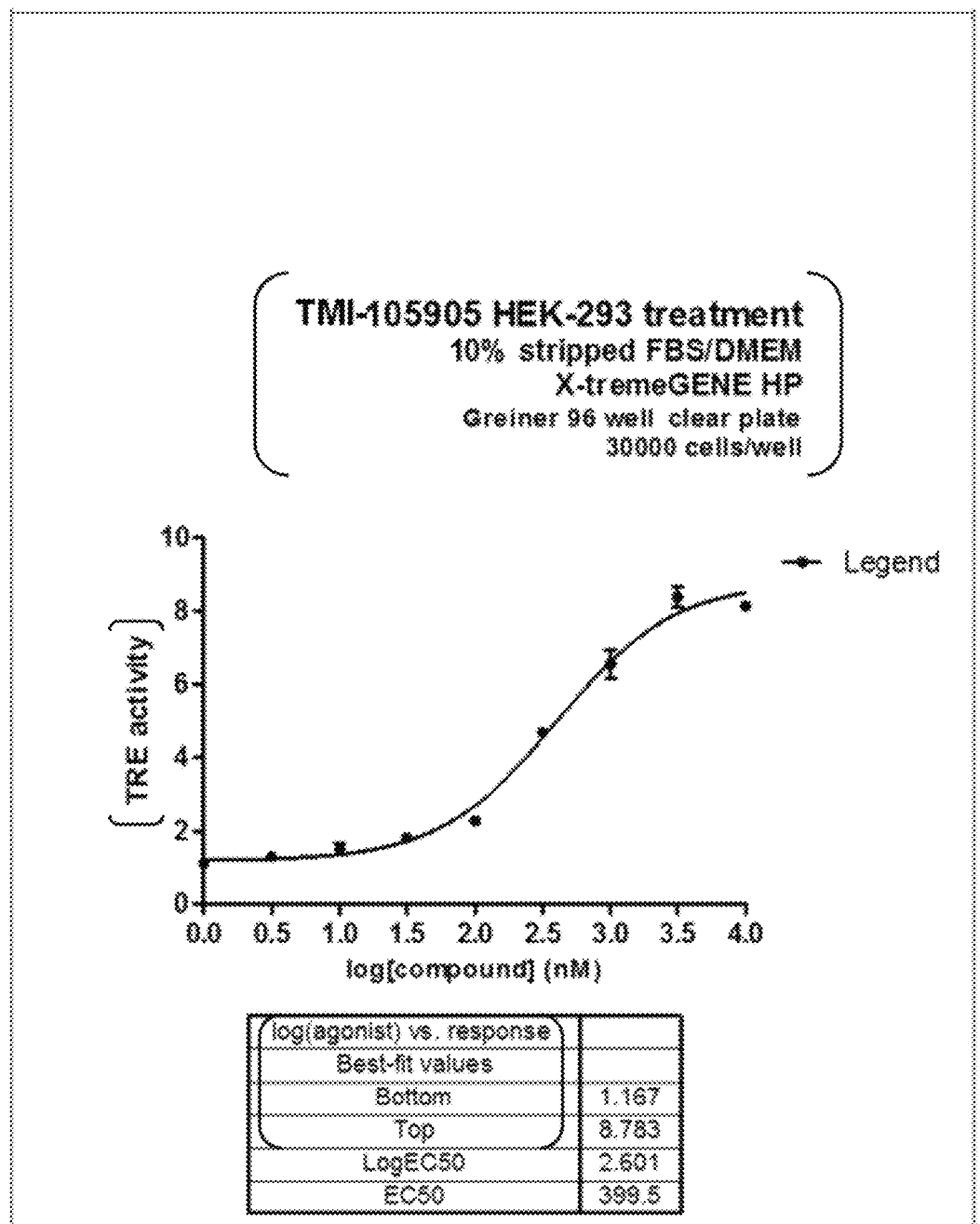
FIG. 5. Experimental results of TMI-105905.
Figure 6:
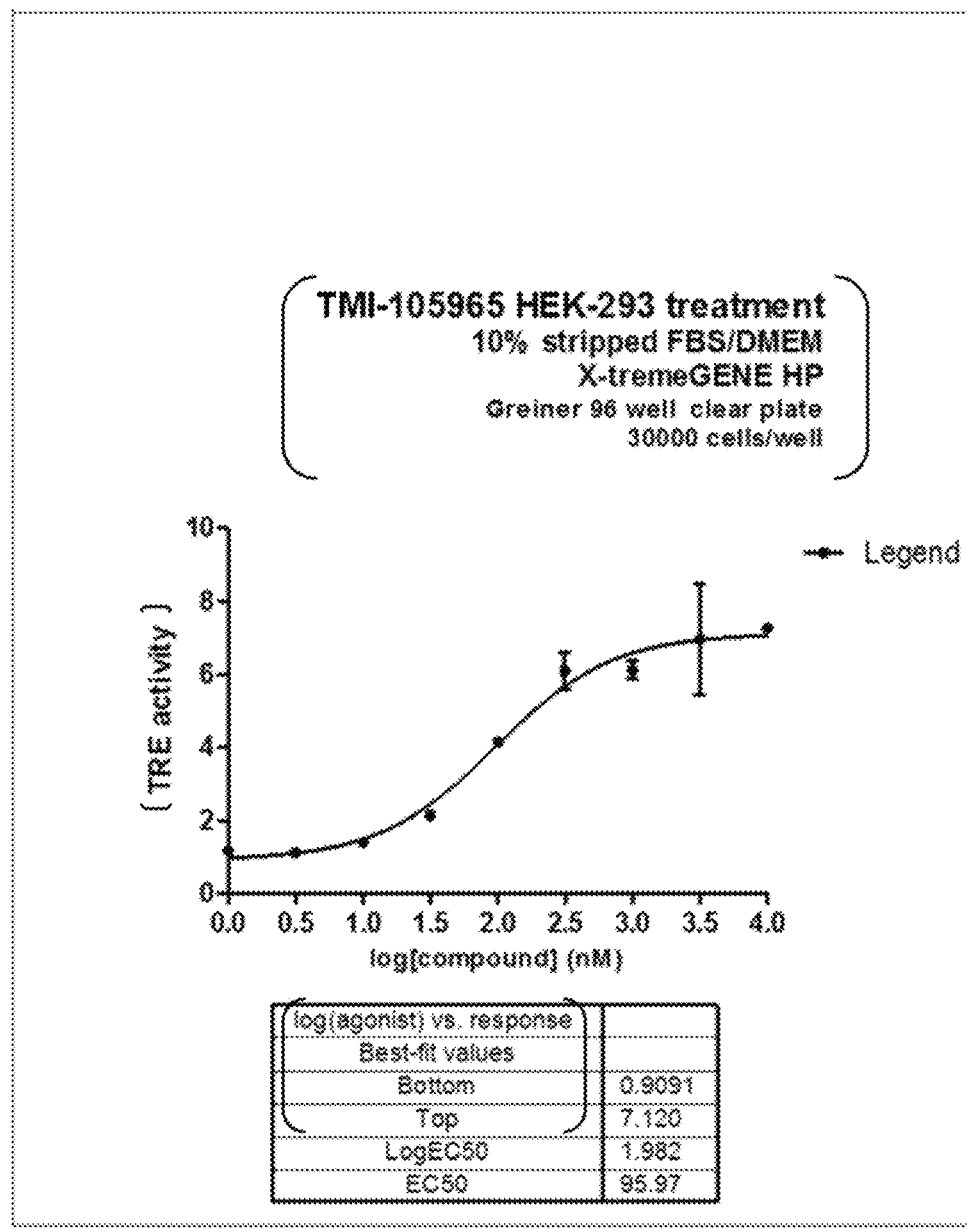
FIG. 6. Experimental results of TMI-105965.
Figure 7:
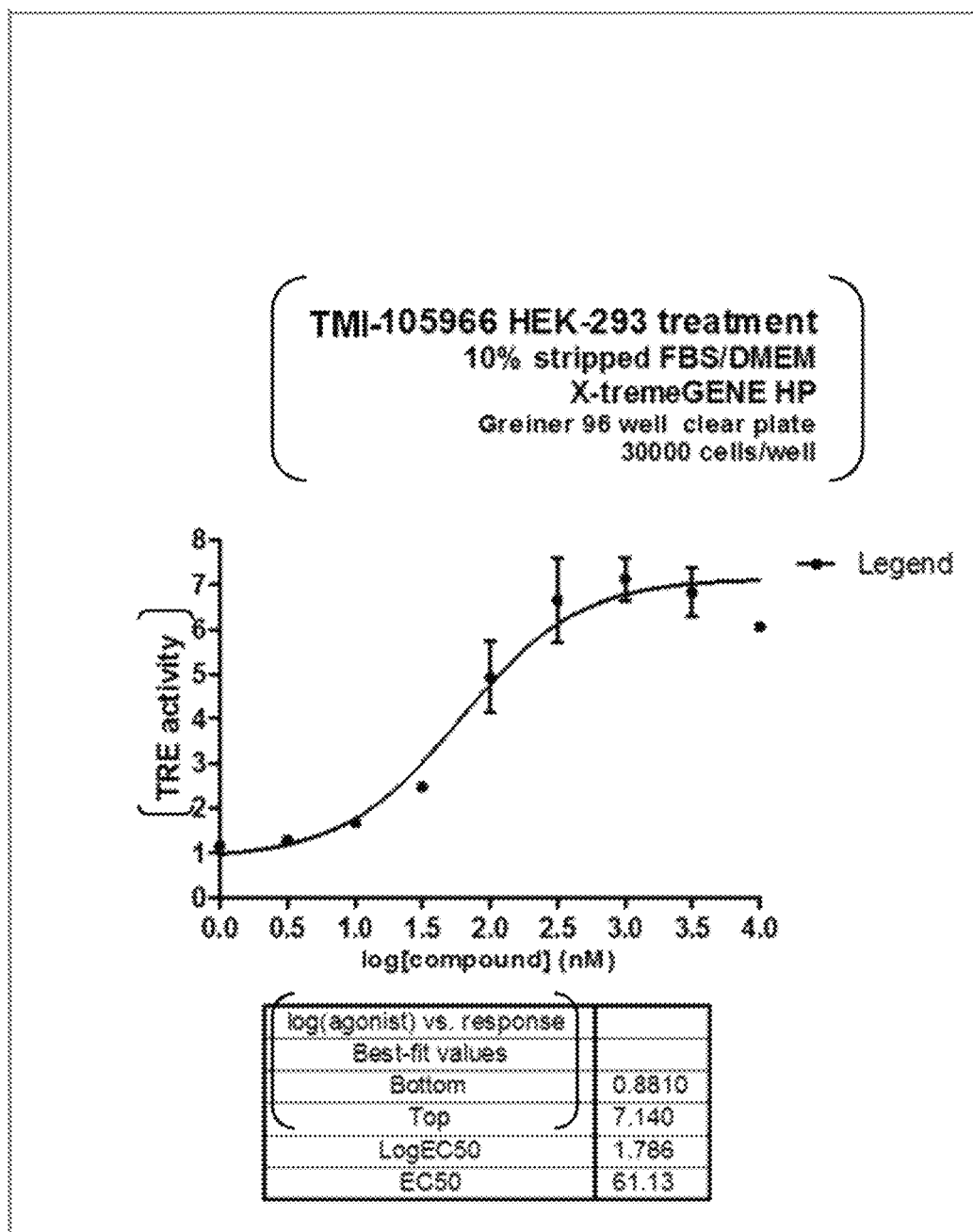
FIG. 7. Experimental results of TMI-105966.
Figure 8:
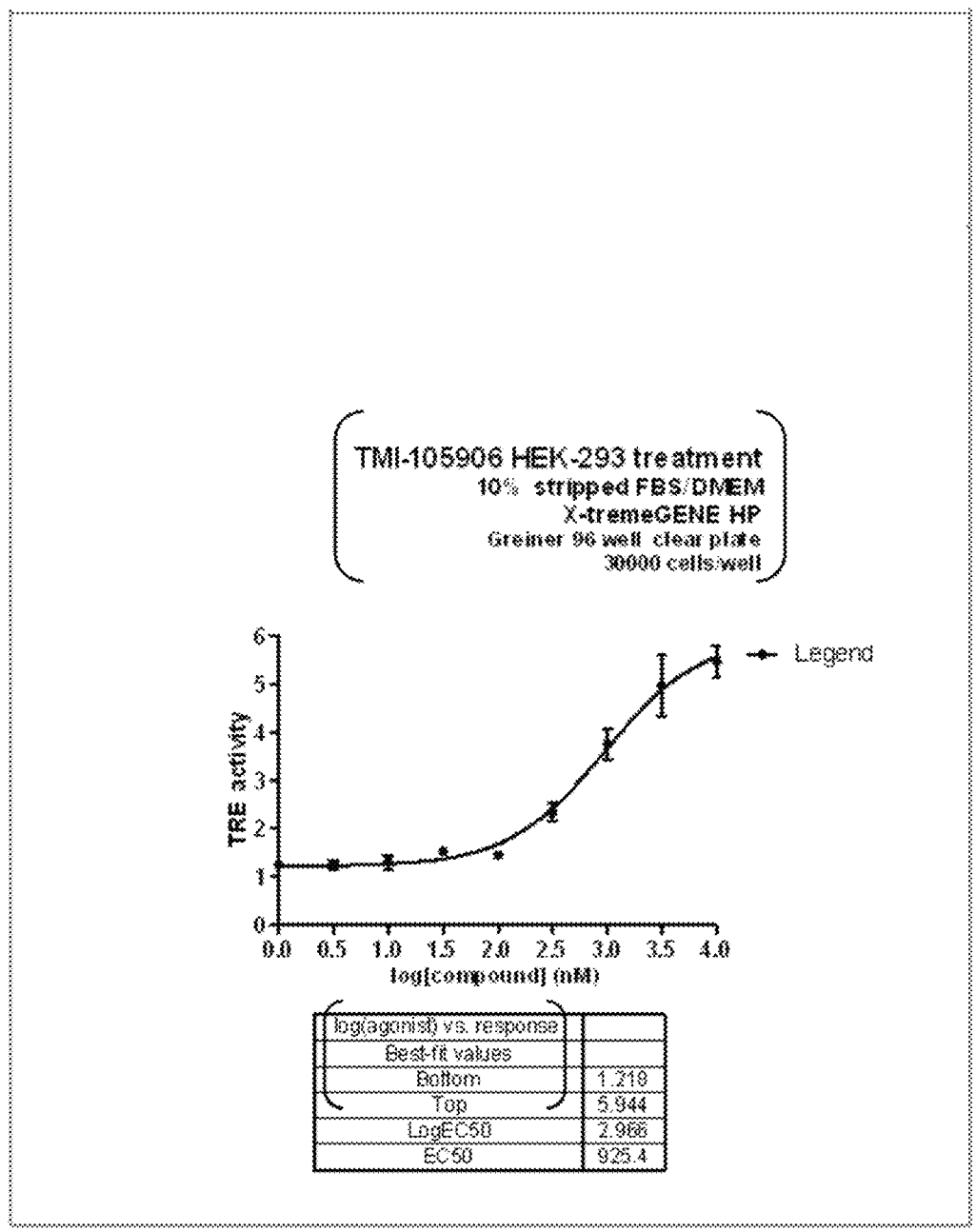
FIG. 8. Experimental results of TMI-105906.
Figure 9:
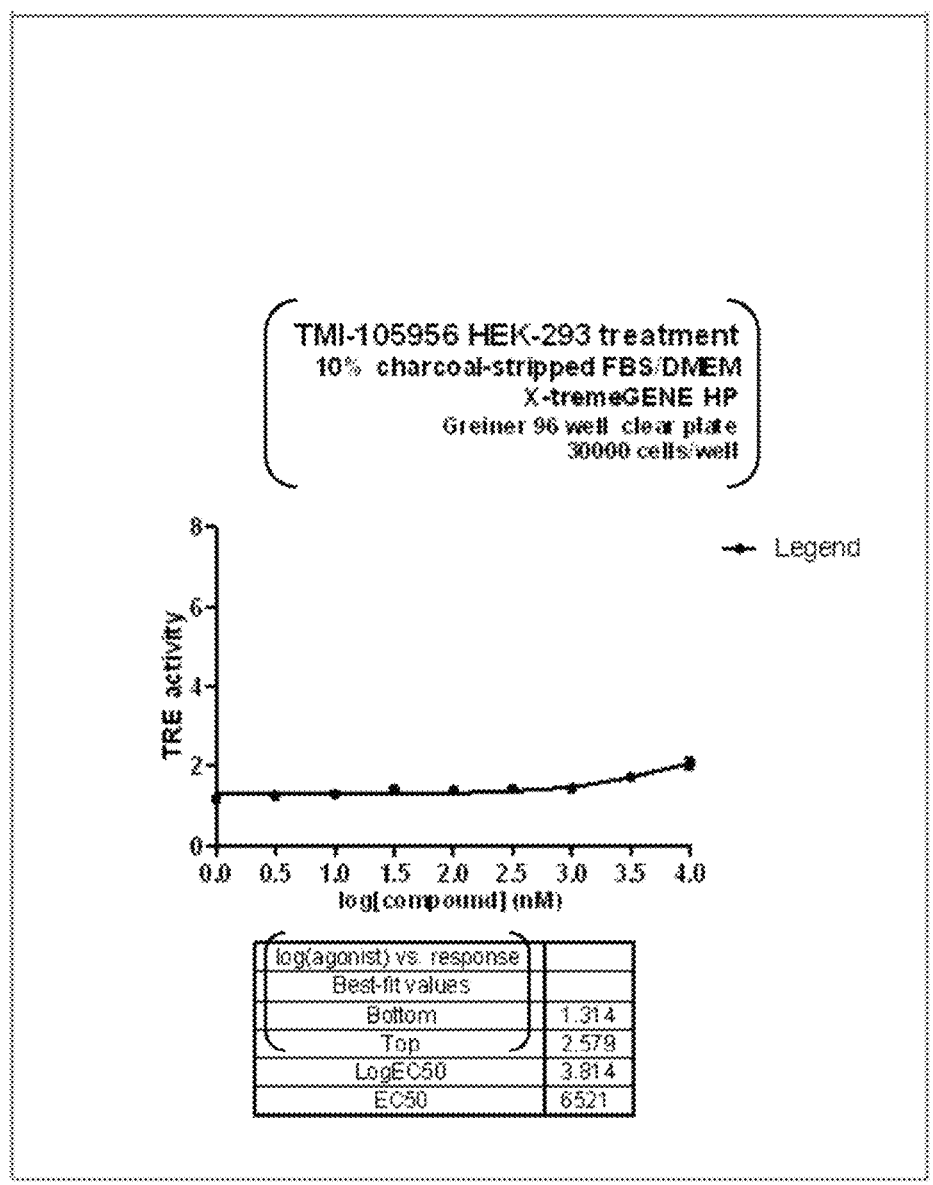
FIG. 9. Experimental results of TMI-105956.
Figure 10:
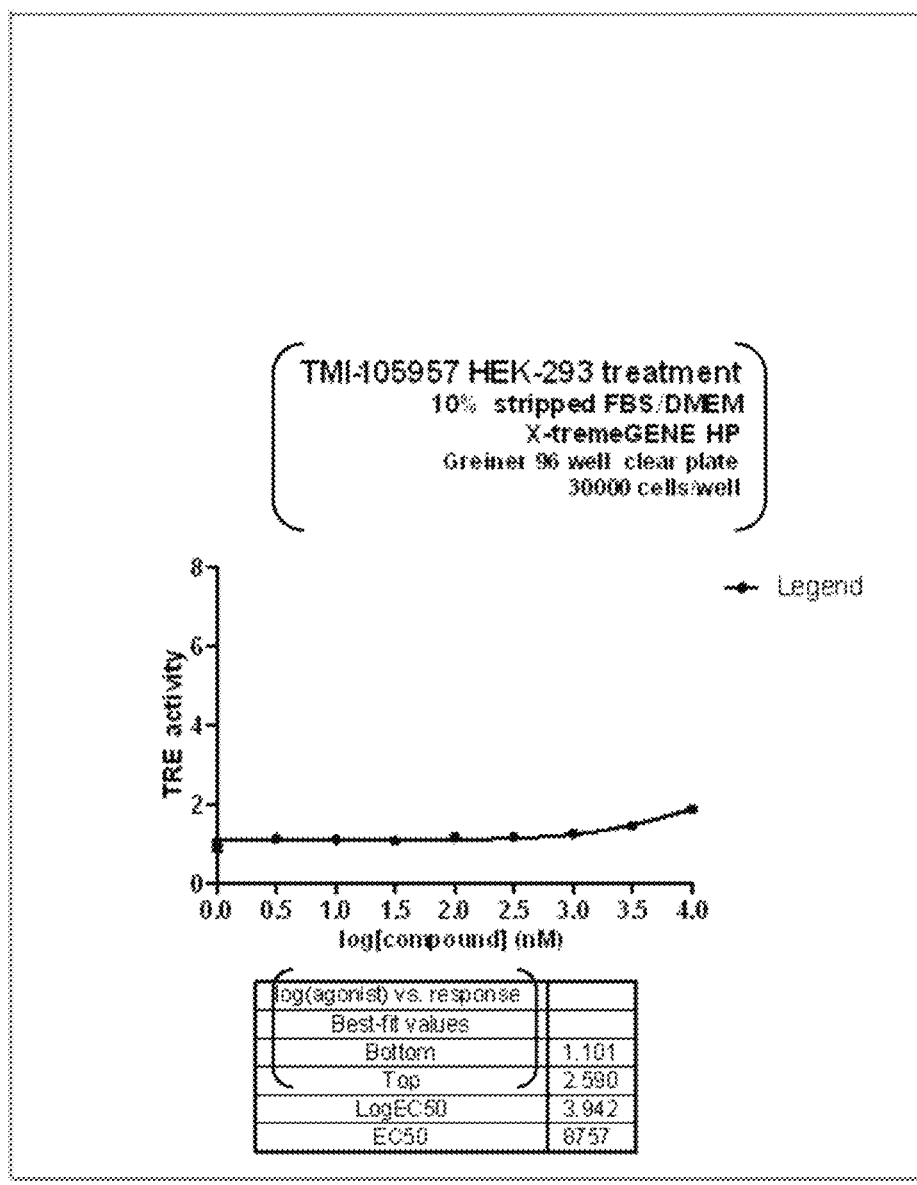
FIG. 10. Experimental results of TMI-105957.
Figure 11:
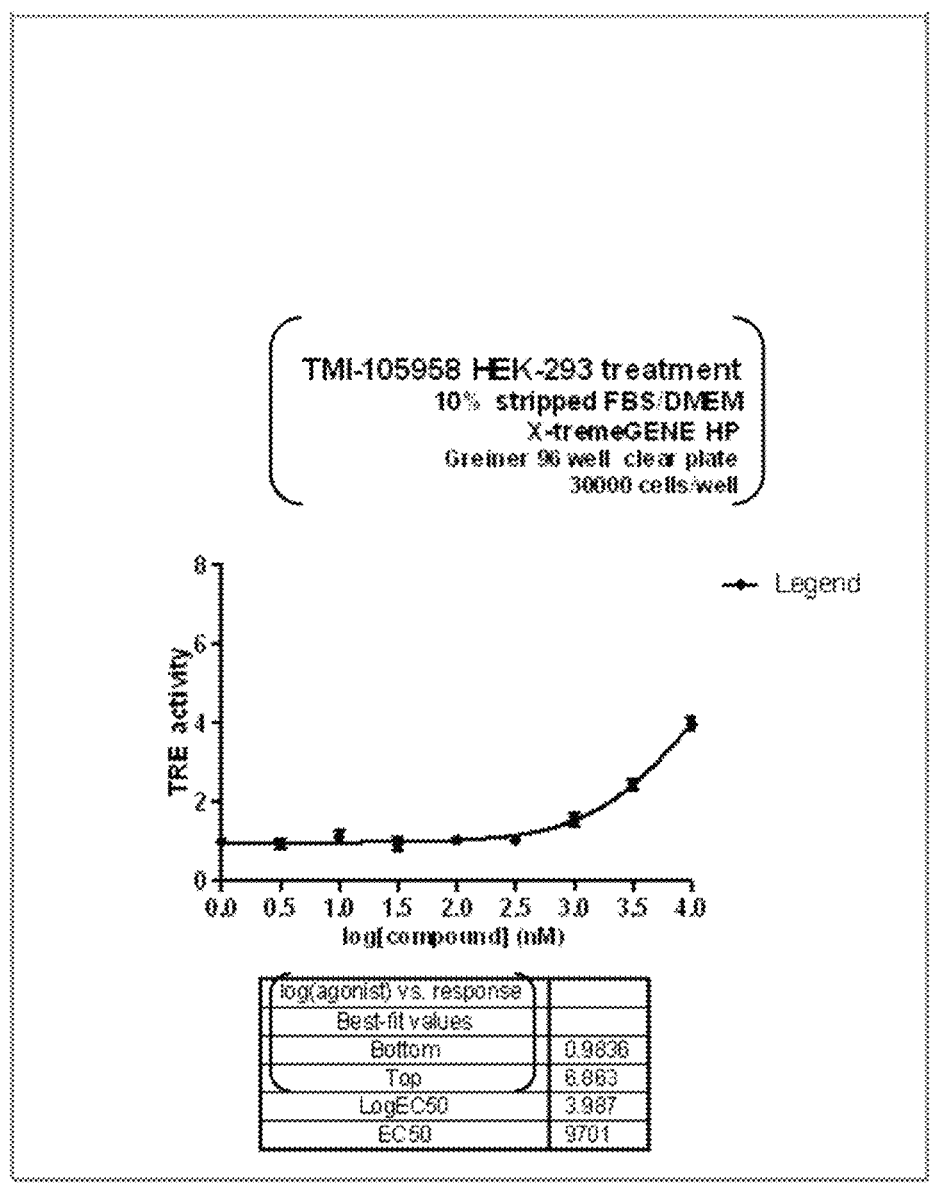
FIG. 11. Experimental results of TMI-105958.
Figure 12:
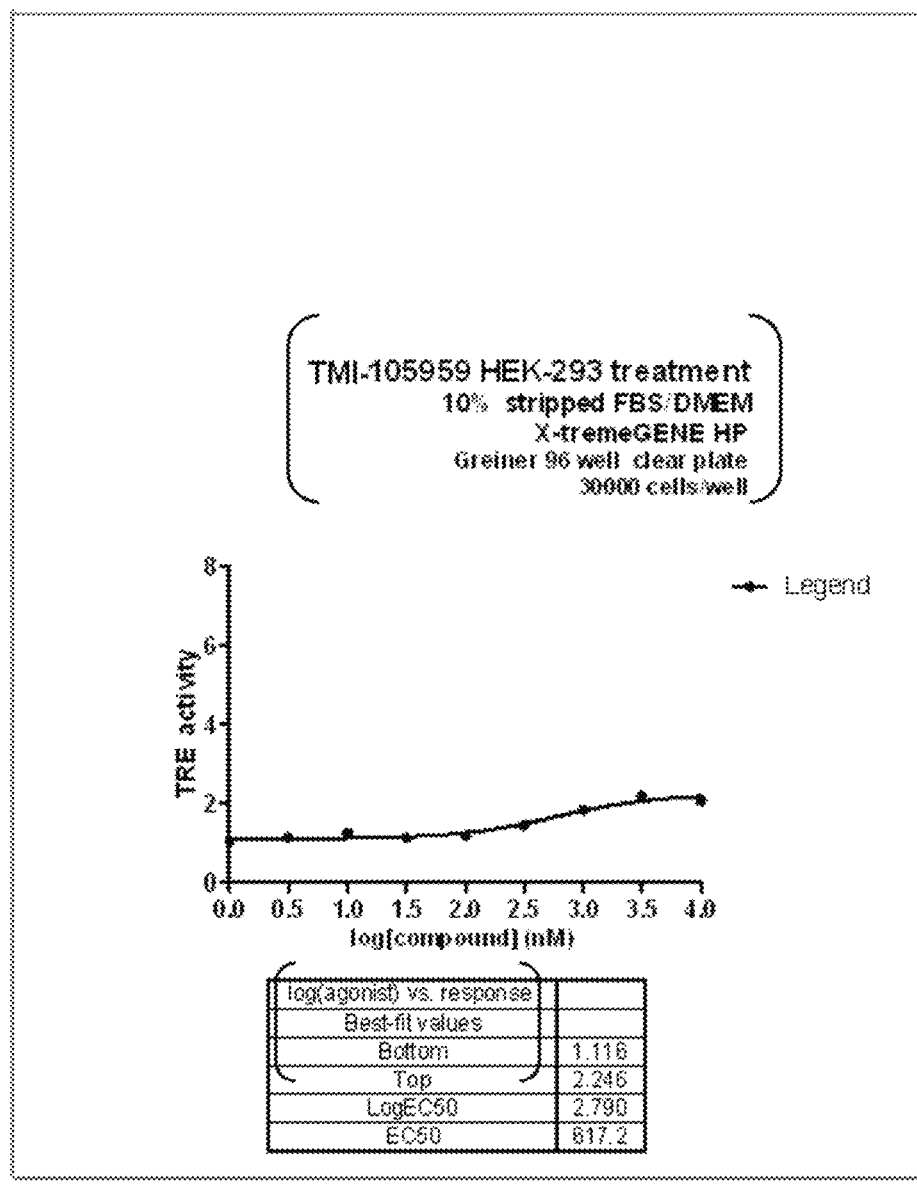
FIG. 12. Experimental results of TMI-105959.
Figure 13:
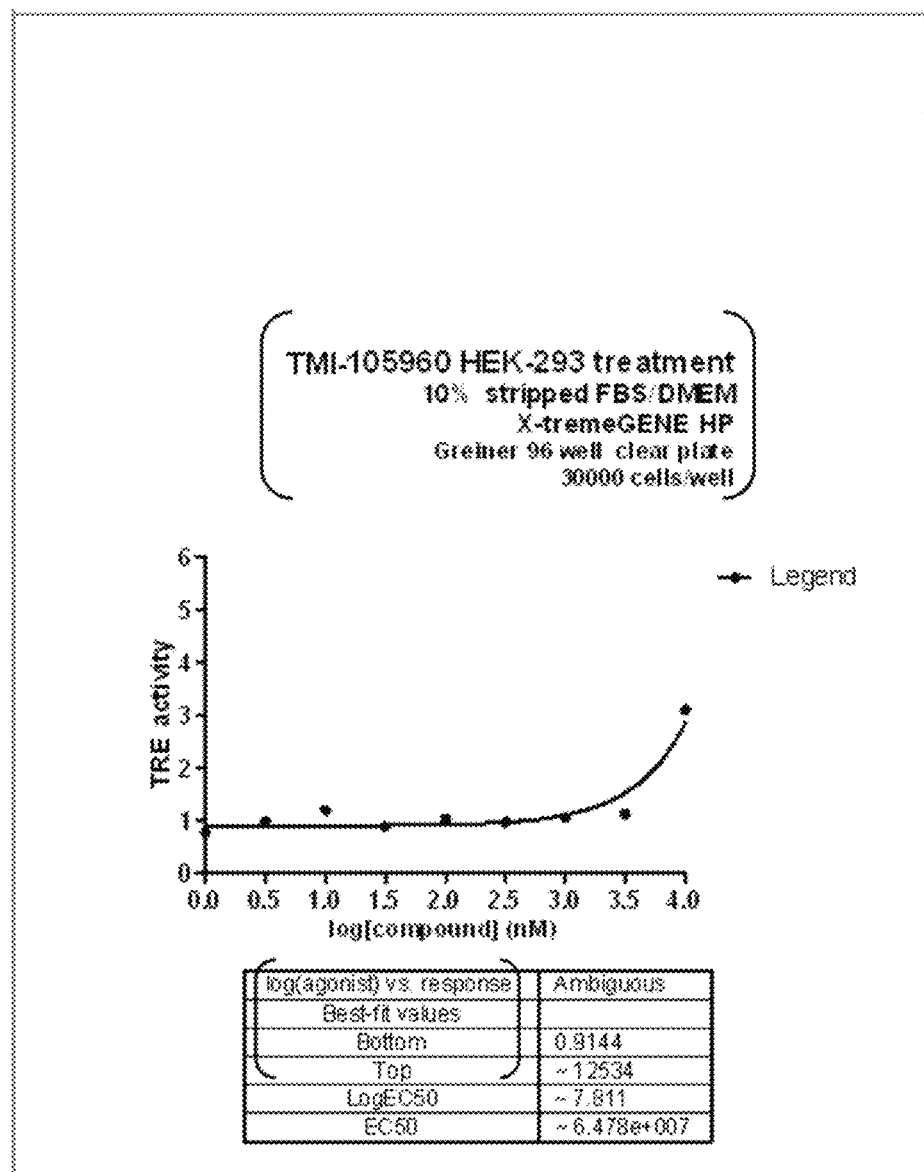
FIG. 13. Experimental results of TMI-105960.
Figure 14:
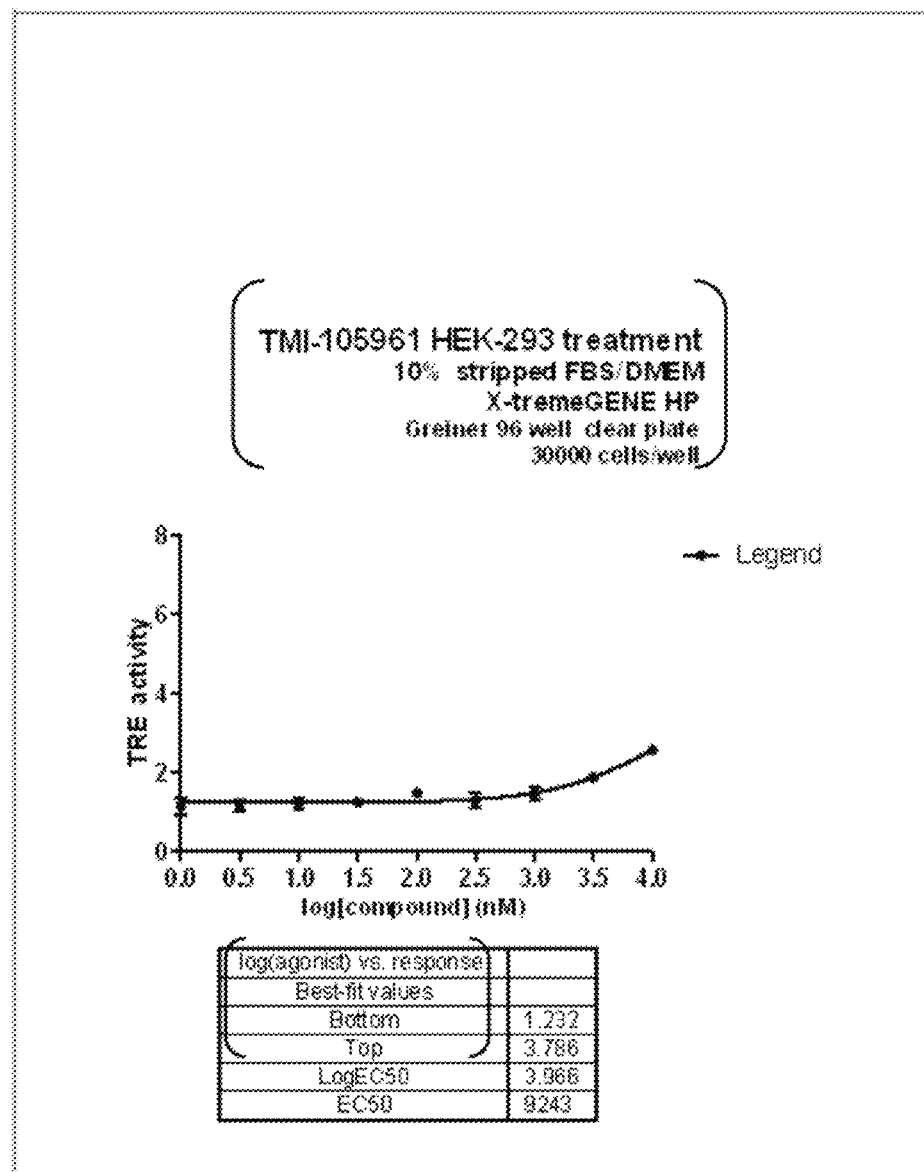
FIG. 14. Experimental results of TMI-105961.
Figure 15:
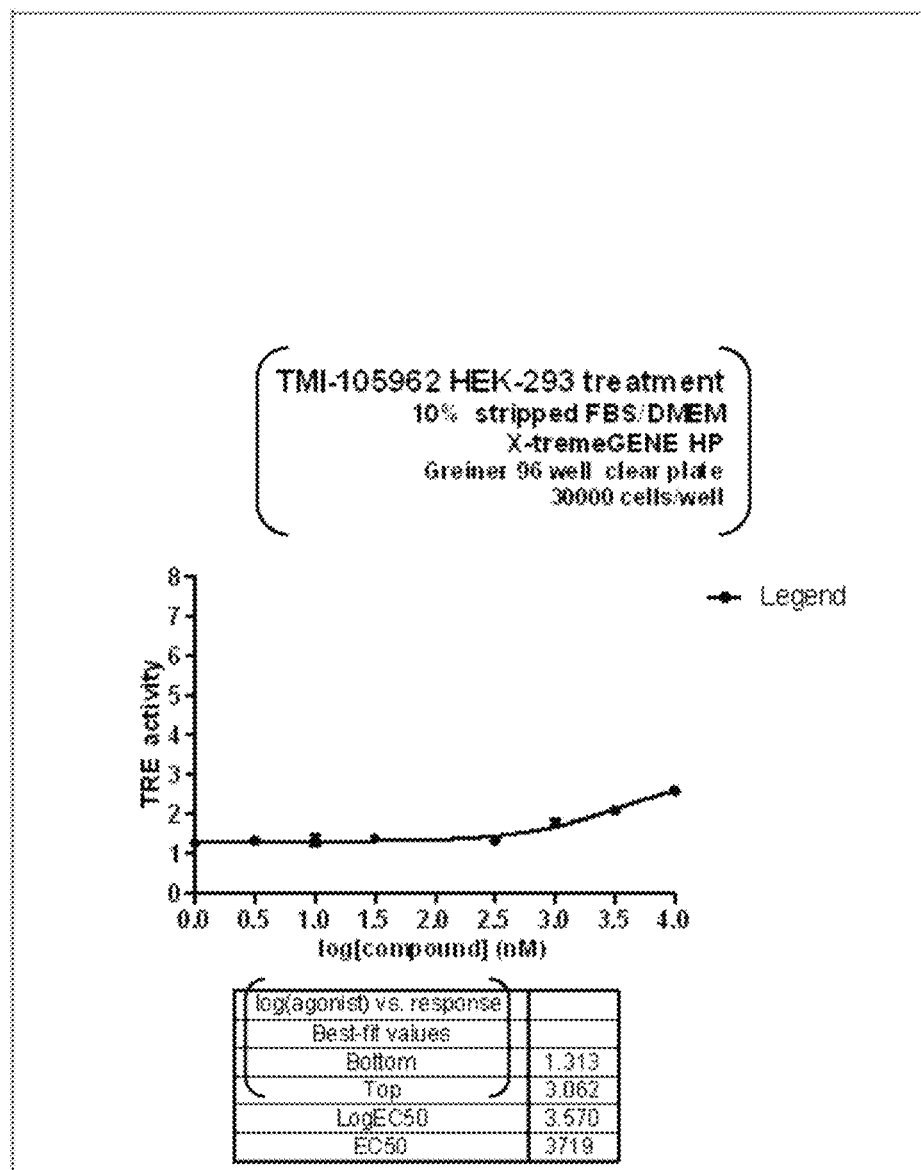
FIG. 15. Experimental results of TMI-105962.
Figure 16:
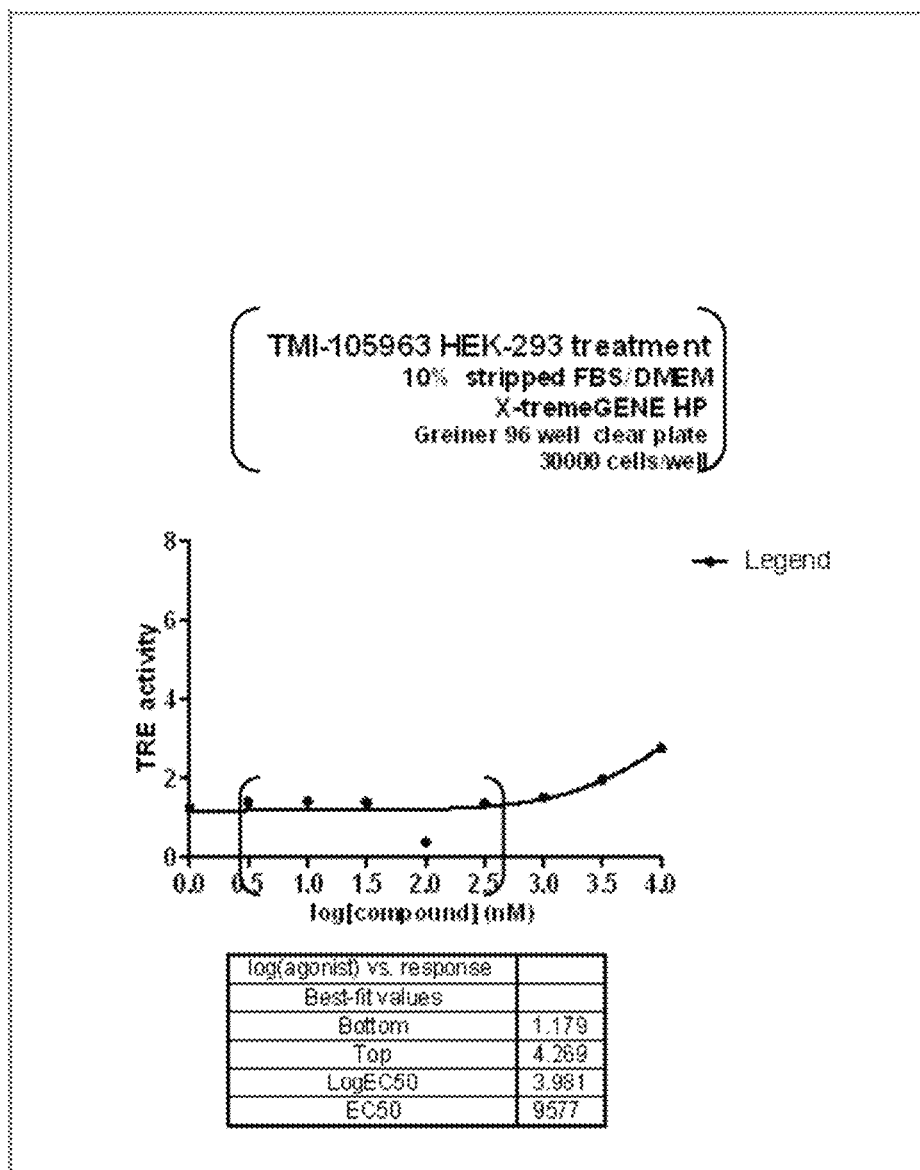
FIG. 16. Experimental results of TMI-105963.

N1-(3,5-dichloro-4-(3-(4-fluorobenzyl)-4-hydroxyphenoxy)phenyl)-N2-oxalyl hydroxylamine Structural Formula:

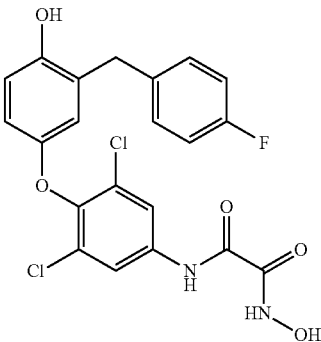 [SMILES: O=C(NO)C(=O)Nc1cc(Cl)c(Oc2ccc(O)c(Cc3ccc(F)cc3)c2)c(Cl)c1]

Synthesizing Route:
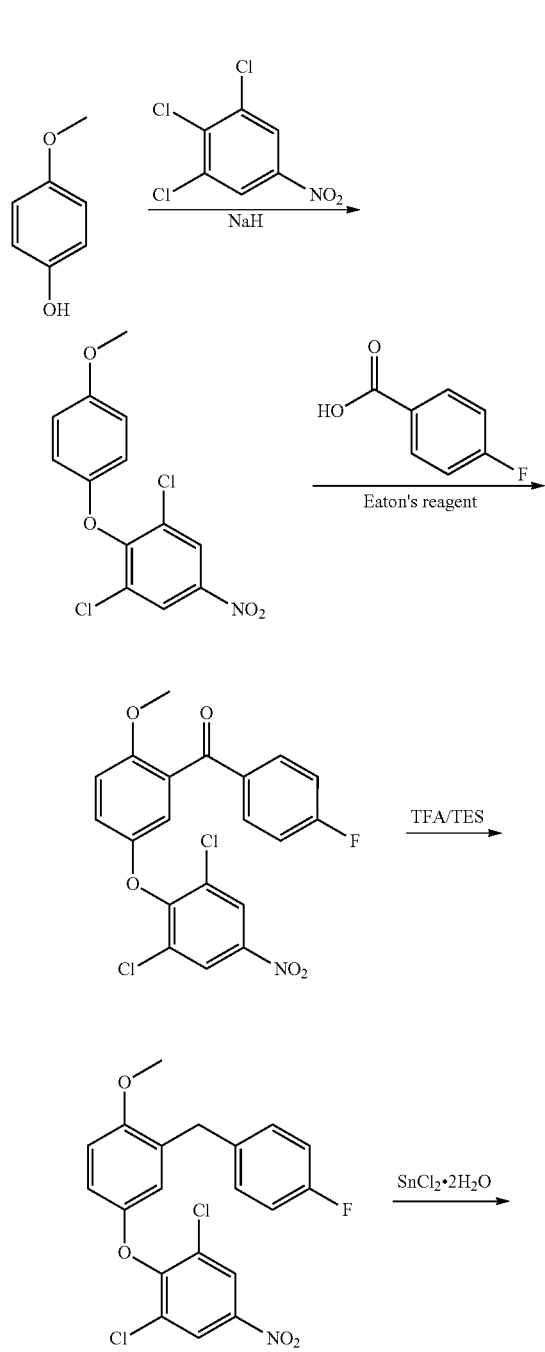
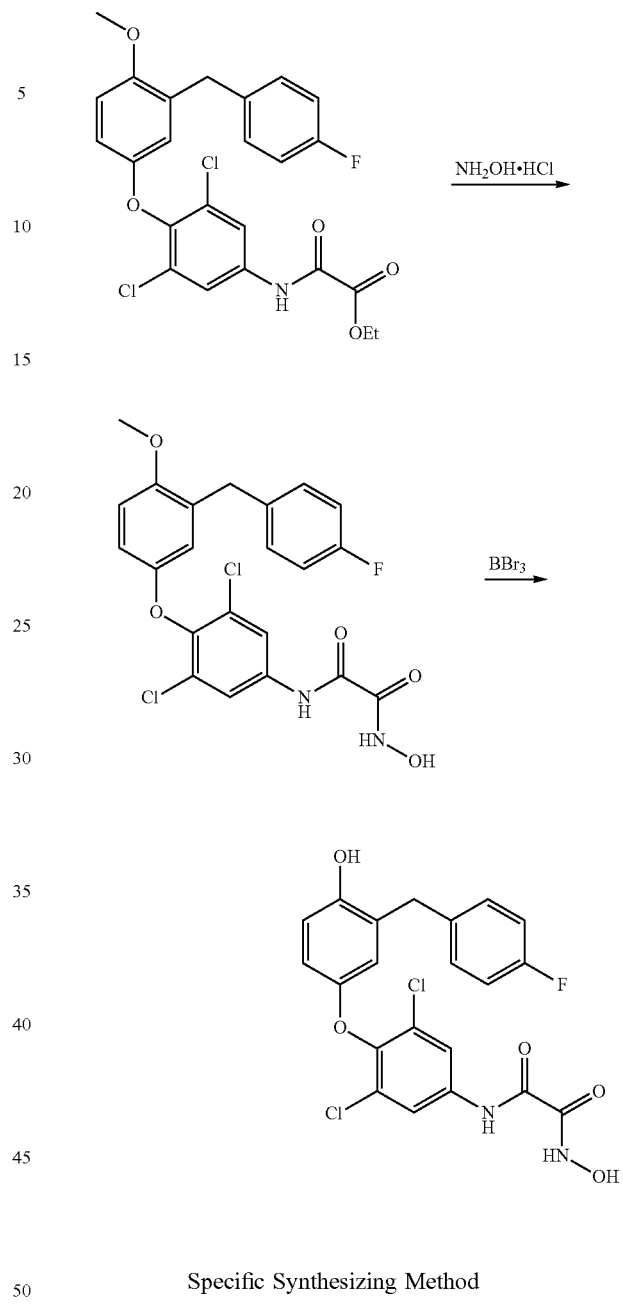
Specific Synthesizing Method
Step 1: Synthesis of
1,3-dichloro-2-(4-methoxyphenoxy)-5-nitrobenzene
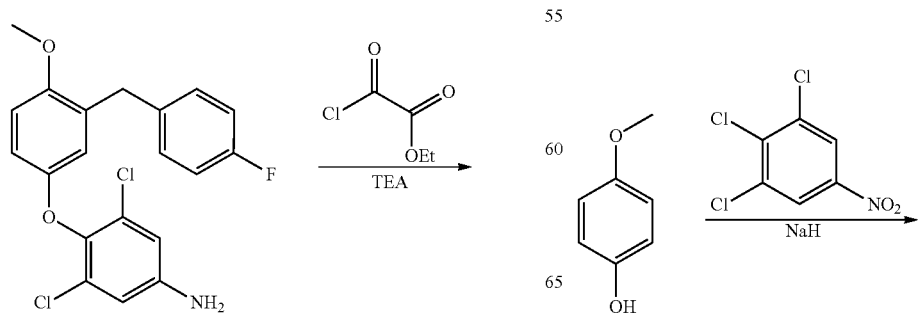

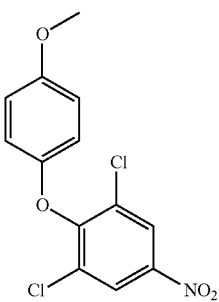

4-methoxyphenol (5.5 g, 44 mmol) was dissolved in DMF (100 mL) and treated with NaH (2.64 g, 66 mmol). After stirring for 30 minutes, 1,2,3-trichloro-5-nitrobenzene (10 g, 44 mmol) was added. The reaction solution was heated to 120° C. for three hours. After completion of reaction, the mixture was cooled to room temperature and then condensed. The residue was quenched with water and extracted with ethyl acetate. The organic layer was dried and concentrated, the crude product was obtained; after column chromatography (0-10% ethyl acetate and petroleum ether), the product was obtained (5.0 g, 36%).

In this step, different reaction conditions are used. For example, different reactant ratio (4-methoxyphenol:NaH:1,2,3-trichloro-5-nitrobenzene=1:2:1 or 1:1.8:1.5, etc.); solvents (chlorobenzene, dioxane, etc); bases (NaH, NaOH, NaOtBu, etc); reaction temperature (130° C., 160° C.); reaction time (1, 2, 4, 5, 6 hours, etc). The reaction yield varies from 31% to 68%.

Step 2: Synthesis of 5-(2,6-dichloro-4-nitrophenoxy)-2-methoxyphenyl)(4-fluorophenyl) methyl ketone

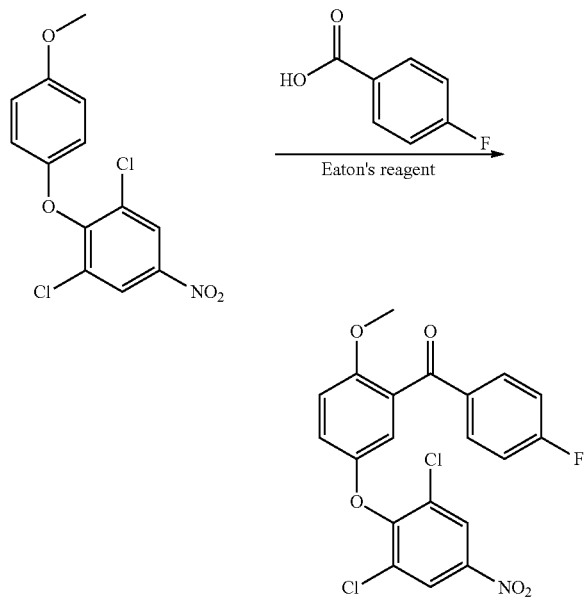

1,3-Dichloro-2-(4-methoxypehnoxy)-5-nitrobenzene (5.0 g, 16 mmol), 4-fluorobenzoic acid (2.8 g, 20 mmol) was distributed in Eaton Reagent (30 mL). The reaction mixture was then heated to 80° C. for 4 hours. After cooling to room temperature, the mixture was quenched with sodium bicarbonate solution. The aqueous phase was extracted with ethyl acetate, dried anhydrously over Na$_2$SO$_4$ and concentrated. The residue was purified on column chromatographically (10% ethyl acetate and petroleum ether). The title compound was obtained (4.5 g, 64%).

In this step, various reaction conditions were also tried, such as reactant ratio (1,3-dichloro-2-(4-methoxyphenoxy)-5-nitrobenzene:4-fluorobenzoic acid=1:1, 1:1.5, 1:2, etc.); reaction temperature (100° C., 110° C., 130° C., etc); reaction time (2, 5, 8 hours, etc). The reaction yield varies from 56% to 78%.

Step 3: Synthesis of 1,3-dichloro-2-(3-(4-fluorobenzyl)-4-methoxyphenoxy)-5-nitrobenzene

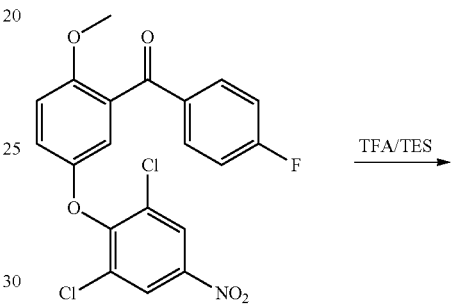

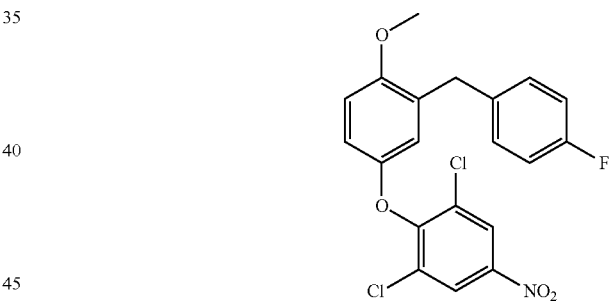

5-(2,6-dichloro-4-nitrophenoxy)-2-methoxyphenyl)(4-fluorophenyl) methyl ketone (4.4 g, 10 mmol) was dissolved in DCM (50 mL) added with trifluoroacetic acid (6.0 g, 40 mmol) and triethyl silane (3.5 g, 30 mmol). The reaction solution was stirred for 3 hours at room temperature. The mixture was quenched with sodium bicarbonate solution. The aqueous phase was extracted with ethyl acetate, dried anhydrously over Na$_2$SO$_4$ and concentrated. The residue was purified on column chromatographically (10% ethyl acetate and petroleum ether). The title compound was obtained (3.5 g, 83%).

In this step, various reaction conditions were also tried, such as reactant ratio (5-(2,6-dichloro-4-nitrophenoxy)-2-methoxyphenyl)(4-fluorophenyl) methyl ketone:trifluoroacetic acid:triethyl silane=1:4:3, 1:5:4, 1:6:5, etc); solvents (chloroform, chlorobenzene, toluene, etc.); reaction time (1, 2, 6 hours, etc.). The reaction yield varies from 80% to 96%.

Step 4: Synthesis of 3,5-dichloro-4-(3-(4-fluorobenzyl)-4-methoxyphenoxy)aniline

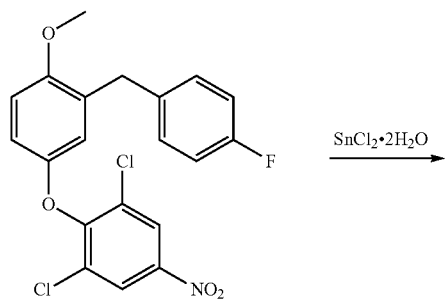

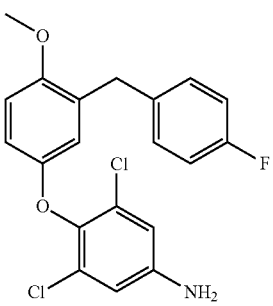

1,3-dichloro-2-(3-(4-fluorobenzyl)-4-methoxyphenoxy)-5-nitrobenzene (3.5 g, 8.3 mmol) was dissolved in ethyl acetate (50 mL), followed by addition of $Sn_2Cl_2$ (18.7 g, 83 mmol). The reaction mixture was heated and refluxed for 3 hours and then cooled to room temperature. The mixture was adjusted to pH 8 using sodium bicarbonate solution and filtered and extracted. After concentration of filtered solution, the product was obtained (2.6 g, 81%).

In this step, various reaction conditions were also tried, such as reactant ratio (1,3-dichloro-2-(3-(4-fluorobenzyl)-4-methoxyphenoxy)-5-nitrobenzene:$Sn_2Cl_2$=1:10, 1:15, 1:20 etc.); solvents (methyl acetate, acetone, benzene, etc); reducing agents (Zn/HCl, Pt/$H_2$, Ni/$H_2$, etc.); reaction time (1, 2, 6 hours, etc.). The reaction yield varies from 80% to 99%.

Step 5: Synthesis of 2-((3,5-dichloro-4-(3-(4-fluorobenzyl)-4-methoxyphenoxy)phenyl)amino)-oxoacetate (ethyl oxalyl)

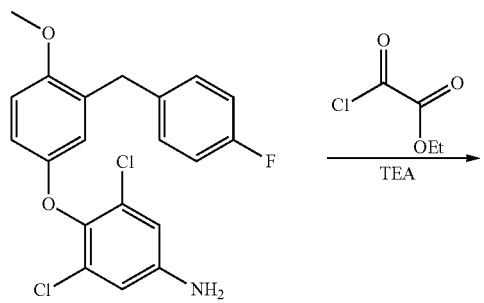

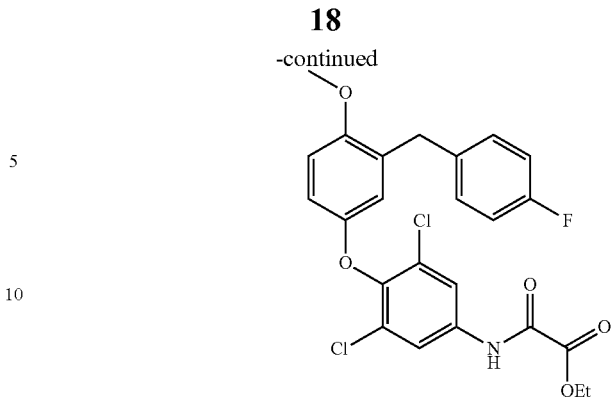

3,5-dichloro-4-(3-(4-fluorobenzyl)-4-methoxyphenoxy)aniline (200 mg, 0.51 mmol) was dissolved in $CH_2Cl_2$ and added with ethyl oxalyl monochloride (120 mg, 0.76 mmol) and triethylamine (100 mg, 1.02 mmol). After one hour of stirring, the reaction mixture was quenched with sodium bicarbonate solution. The aqueous phase was extracted with $CH_2Cl_2$ and the organic layer was washed with saturated brine and dried anhydrously over $Na_2SO_4$. After concentration, the product was obtained (250 mg, 100%).

In this step, various reaction conditions were also tried, such as reactant ratio (the molar ratio of 3,5-dichloro-4-(3-(4-fluorobenzyl)-4-methoxyphenoxy)aniline:ethyl oxalyl monochloride=1:1.5, 1:2, 1:2.3, 1:3, etc, ethyl oxalyl monochloride:triethylamine=1:1.5, 1:2, 1:2.3, etc.); solvents (chloroform, ethyl acetate, chlorobenzene, etc.); reaction time (0.5, 2, 3 hours, etc). The reaction yield varies from 90%-100%.

Step 6: Synthesis of N1-(3,5-dichloro-4-(3-(4-fluorobenzyl)-4-methoxyphenoxy)phenyl)-N2-oxalyl hydroxylamine

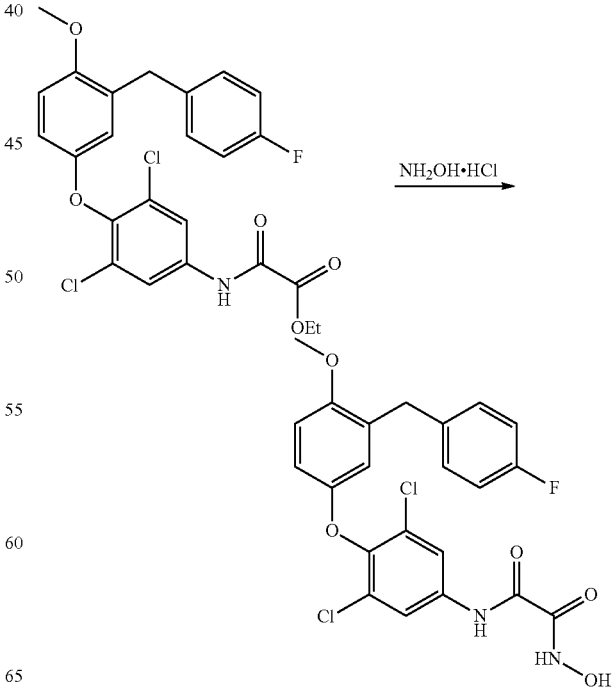

2-((3,5-dichloro-4-(3-(4-fluorobenzyl)-4-methoxyphenoxy) phenyl)amino)-oxoacetate (ethyl oxalyl) (50 mg, 0.10 mmol), hydroxylamine hydrochloride (35 mg, 0.5 mmol) and NaOH (20 mg, 0.5 mmol) were dissolved in Ethanol (EtOH) (10 mL). The reaction mixture was stirred at room temperature overnight. After removal of solvent, the residue was extracted with ethyl acetate. After drying and concentration, the title compound was obtained (50 mg, 100%).

In this step, various reaction conditions were also tried, such as reactant ratio (the molar ratio of 2-((3,5-dichloro-4-(3-(4-fluorobenzyl)-4-methoxyphenoxy)phenyl)-amino)-oxoacetate (ethyl oxalyl): hydroxylamine hydrochloride: NaOH=1:4:4; 1:6:6; 1:8:8, 1:10:10, etc.); solvents (ethyl acetate, Methanol (MeOH), etc); reaction time (8, 10, 12, 14, 16,d 18 hours, etc). The reaction yield varies from 90% to 100%.

Step 7: Synthesis of N1-(3,5-dichloro-4-(3-(4-fluorobenzyl)-4-hydroxyphenoxy)phenyl)-N2-oxalyl hydroxylamine

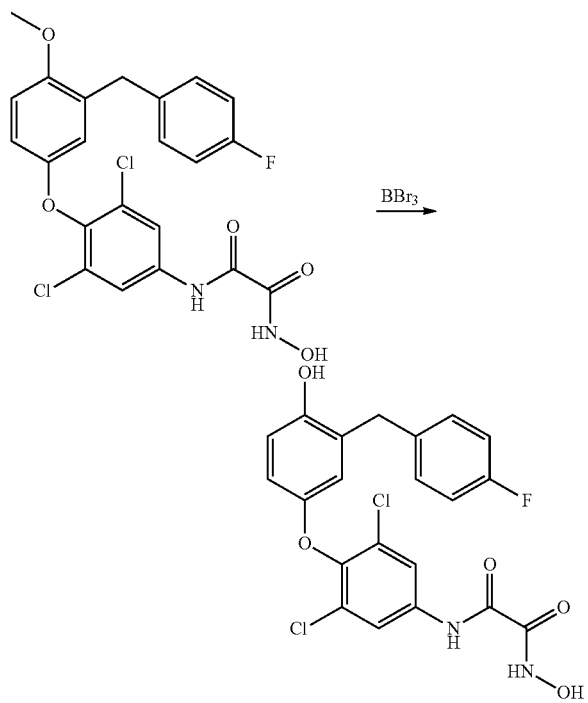

N1-(3,5-dichloro-4-(3-(4-fluorobenzyl)-4-methoxyphenoxy) phenyl)-N2-oxalyl hydroxylamine (50 mg, 0.1 mmol) was dissolved in $CH_2Cl_2$ and added with 2 drops of $BBr_3$. The reaction mixture was stirred for 3 hours followed by MeOH quenching. The residues are dispersed in ethyl acetate and water, after concentration of ethyl acetate layer, n-hexane is added and the product is separated out (6 mg, 12%).

In this step, various reaction conditions were also tried, such as $BBr_3$ (1 mg, 5 mg, 10 mg, 15 mg, 20 mg, etc); solvents ($CH_2Cl_2$, $CHCl_3$ and $CCl_4$, etc); reaction time (1, 2, 5 hours, etc). The reaction yield varies from 4% to 30%.
Spectrum Data of Product:
$H^1$-NMR (MeOD) δ 7.92 (s, 2H), 7.19 (dd, J=8.7, 5.5 Hz, 2H), 6.96 (t, J=8.9 Hz, 2H), 6.71 (d, J=9.1 Hz, 1H), 6.44-6.51 (m, 2H), 3.87 (s, 2H) Mass Spectrum: m/z 465.3 $[M+H]^+$ The following synthesizing methods used in Examples 2-6 are similar or close to that in Example 1, and they are not repeated herein accordingly.

Example 2 Product Number: TMI-105902

Name

N1-(3,5-dichloro-4-(3-(4-methylsulphonylbenzyl)-4-hydroxyphenoxy)phenyl)-N2-oxalyl hydroxylamine Structural Formula:

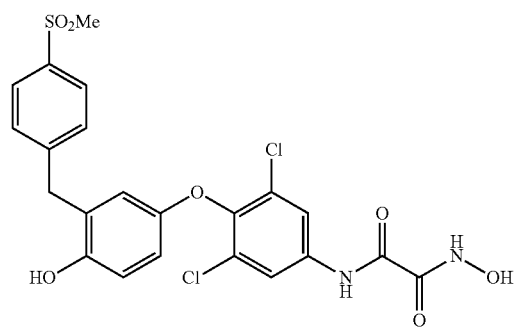 [SMILES: CS(=O)(=O)c1ccc(Cc2cc(Oc3c(Cl)cc(NC(=O)C(=O)NO)cc3Cl)ccc2O)cc1]

Spectrum Data of Product
$^1$H NMR (MeOD) δ 7.92 (s, 2H), 7.83 (d, J=8.6 Hz, 2H), 7.47 (d, J=8.3 Hz, 2H), 6.73 (d, J=9.4 Hz, 1H), 6.49-6.57 (m, 2H), 4.02 (s, 2H), 3.10 (s, 3H)

Mass Spectrum: m/z 523.6$[M-H]^-$

Example 3 Product Number: TMI-105903

Name

N1-(3,5-dichloro-4-(3-(4-methylbenzyl)-4-hydroxyphenoxy)phenyl)-N2-oxalyl hydroxylamine Structural Formula:

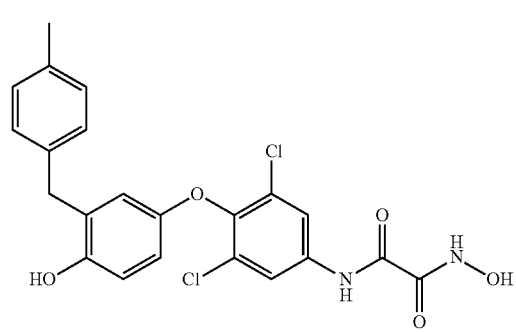 [SMILES: Cc1ccc(Cc2cc(Oc3c(Cl)cc(NC(=O)C(=O)NO)cc3Cl)ccc2O)cc1]

Spectrum Data of Product:
$^1$H NMR (MeOD) δ 7.90 (s, 2H), 7.05 (s, 4H), 6.70 (d, J=8.6 Hz, 1H), 6.43-6.49 (m, 1H), 6.39 (d, J=3.0 Hz, 1H), 3.84 (s, 2H), 2.29 (s, 3H)

Mass Spectrum: m/z 459.6$[M-H]^-$

Example 4 Product Number: TMI-105905

Name

N1-(3,5-dichloro-4-(3-(3,4-dichlorobenzyl)-4-hydroxyphenoxy)phenyl)-N2-oxalyl hydroxylamine Structural Formula:

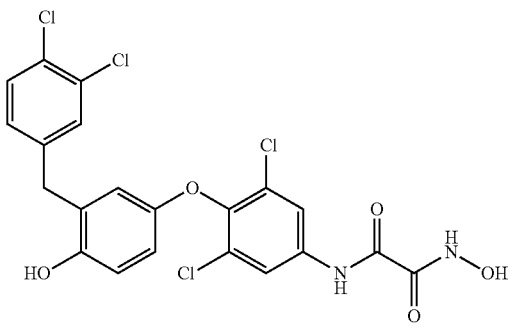 [SMILES: O=C(NO)C(=O)Nc1cc(Cl)c(Oc2ccc(O)c(Cc3ccc(Cl)c(Cl)c3)c2)c(Cl)c1]

Spectrum Data of Product $^1$H NMR (MeOD) δ 7.93 (s, 2H), 7.38 (d, J=8.1 Hz, 1H), 7.32 (d, J=1.9 Hz, 1H), 7.12 (dd, J=8.2, 2.0 Hz, 1H), 6.73 (d, J=8.6 Hz, 1H), 6.52-6.58 (m, 1H), 6.50 (d, J=3.0 Hz, 1H), 3.87 (s, 2H)

Mass Spectrum: m/z 513.5[M−H]$^-$

Example 5 Product Number TMI-105965

Name

N1-(3,5-dichloro-4-(3-(3-fluorobenzyl)-4-methoxyphenoxy)phenyl)-N2-oxalyl hydroxylamine Structural Formula:

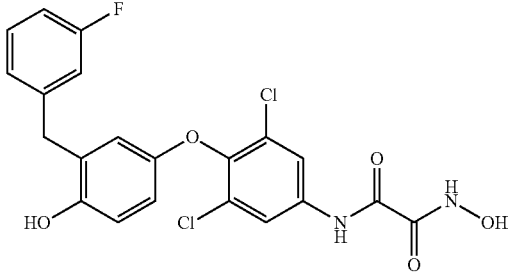 [SMILES: O=C(NO)C(=O)Nc1cc(Cl)c(Oc2ccc(O)c(Cc3cccc(F)c3)c2)c(Cl)c1]

Spectrum Data of Product:

$^1$H NMR (MeOD) δ 7.91 (s, 2H), 7.11-7.24 (m, 2H), 6.98-7.08 (m, 2H), 6.71 (d, J=8.6 Hz, 1H), 6.48 (dd, J=8.6, 3.2 Hz, 1H), 6.42 (d, J=3.0 Hz, 1H), 3.91 (s, 2H)

Mass Spectrum: m/z 463.5[M−H]$^-$

Example 6 Product Number: TMI-105966

Name

N1-(3,5-dichloro-4-(3-(2-fluorobenzyl)-4-methoxyphenoxy)phenyl)-N2-oxalyl hydroxylamine Structural Formula:

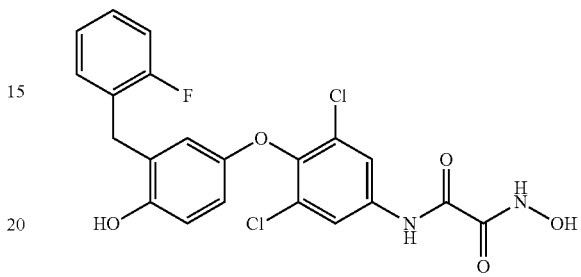

Spectrum Data of Product:

$^1$H NMR (MeOD) δ 7.91 (s, 2H), 7.12-7.24 (m, 2H), 7.00-7.10 (m, 2H), 6.71 (d, J=8.6 Hz, 1H), 6.48 (dd, J=8.7, 3.1 Hz, 1H), 6.42 (d, J=3.0 Hz, 1H), 3.91 (s, 2H) Mass Spectrum: m/z 463.5[M−H]$^-$ Example 7 Product Number: TMI-105906

Name

N1-(3,5-dichloro-4-(4-hydroxy-3-(morpholinomethyl)phenoxy)phenyl)-N2-oxalyl hydroxylamine Structural Formula:

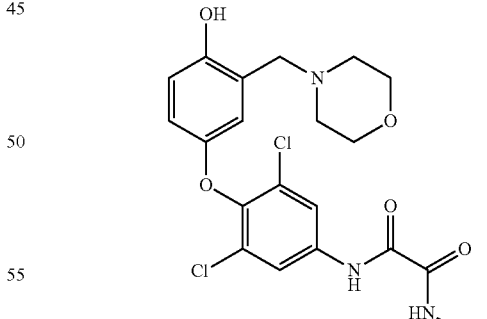

Spectrum Data of Product $^1$H NMR (DMSO-d$_6$) δ: 10.99 (br. s., 1H), 9.83 (br. s., 2H), 8.95 (s, 1H), 7.96-8.22 (m, 2H), 7.60-7.73 (m, 1H), 6.64-6.72 (m, 2H), 6.51-6.60 (m, 1H), 3.57 (br. s., 4H), 3.52 (s, 2H), 2.40 (br. s., 4H)

Example 8 Product Number: TMI-105956

Name

N1-(3,5-dichloro-4-(4-hydroxy-3-(4-hydropiperidine-1-yl)phenoxy)phenyl)-N2-oxalyl hydroxylamine Structural Formula:

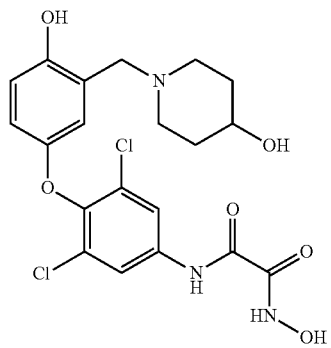 [SMILES: O=C(NO)C(=O)Nc1cc(Cl)c(Oc2ccc(O)c(CN3CCC(O)CC3)c2)c(Cl)c1]

Spectrum Data of Product:

$^1$H NMR (DMSO-d$_6$) δ: δ: 10.10 (br. s., 1H), 8.10 (s, 3H), 6.58-6.73 (m, 2H), 6.53 (d, J=8.3 Hz, 1H), 4.62 (br. s., 1H), 3.37 (br. s., 2H), 2.69 (br. s., 2H), 2.14 (br. s., 2H), 1.72 (d, J=9.4 Hz, 2H), 1.38 (d, J=9.1 Hz, 2H)

Example 9 Product Number TMI-105957

Name

N1-(3,5-dichloro-4-(4-hydroxy-3-(4-methylpiperazine-1-methyl)phenoxy)phenyl)-N2-oxalyl hydroxylamine Structural Formula:

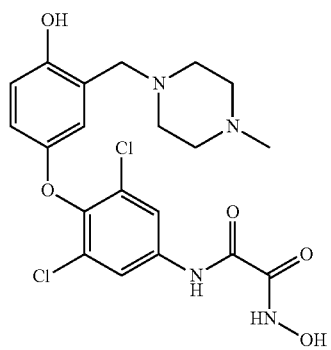 [SMILES: CN1CCN(Cc2cc(Oc3c(Cl)cc(NC(=O)C(=O)NO)cc3Cl)ccc2O)CC1]

Spectrum Data of Product:

$^1$H NMR (DMSO-d$_6$) δ: 11.01 (br. s., 1H), 8.06-8.14 (m, 2H), 6.60-6.70 (m, 2H), 6.54 (dd, J=8.7, 3.1 Hz, 1H), 3.34 (br. s., 2H), 2.42 (br. s., 4H), 2.18-2.38 (m, 4H), 2.11-2.18 (m, 3H)

Example 10 Product Number: TMI-105958

Name

N1-(3,5-dichloro-4-(4-hydroxy-3-(methylpyrrolidin-1-methyl)phenoxy)phenyl)-N2-oxalyl hydroxylamine Structural Formula:

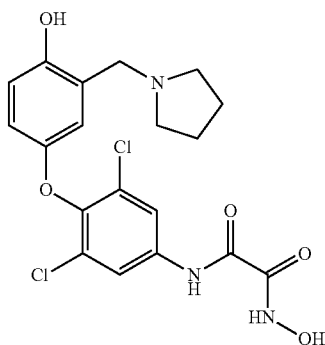 [SMILES: O=C(NO)C(=O)Nc1cc(Cl)c(Oc2ccc(O)c(CN3CCCC3)c2)c(Cl)c1]

Spectrum Data of Product:

$^1$H NMR (DMSO-d$_6$): δ: 10.90 (br.s., 1H), 10.77 (br.s., 1H), 8.11 (br.s., 2H), 6.87 (br.s., 1H), 6.64 (br.s., 2H), 6.53 (br.s., 2H), 3.45 (d, J=5.4 Hz, 2H), 1.72 (br.s., 4H), 1.06 (br.s., 2H)

Example 11 Product Number: TMI-105969

Name

N1-(4-(3-((4-benzylpiperidin-1-methyl)-4-hydroxyphenoxy)-3,5-dichlorophenyl)-N2-oxalyl hydroxylamine Structural Formula:

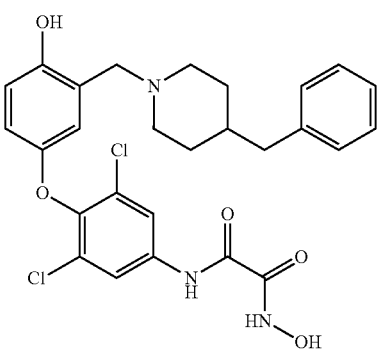 [SMILES: O=C(NO)C(=O)Nc1cc(Cl)c(Oc2ccc(O)c(CN3CCC(Cc4ccccc4)CC3)c2)c(Cl)c1]

Spectrum Data of Product:

$^1$H NMR (METHANOL-d$_4$) δ: 8.40 (br. s., 1H), 7.99 (s, 2H), 7.51 (d, J=7.3 Hz, 2H), 7.38 (t, J=7.5 Hz, 2H), 7.30 (d, J=7.5 Hz, 1H), 6.87-6.98 (m, 2H), 6.82-6.87 (m, 1H), 4.34 (s, 2H), 3.38-3.52 (m, 4H), 2.28-2.41 (m, 2H), 1.96 (d, J=14.2 Hz, 3H), 1.27-1.39 (m, 2H)

Example 12 Product Number: TMI-105960

Name

N1-(3,5-dichloro-4-(4-hydroxy-3-((4-hydroxy-4-phenylpiperidin-1-methyl)phenoxy)phenyl)-N2-oxalyl hydroxylamine

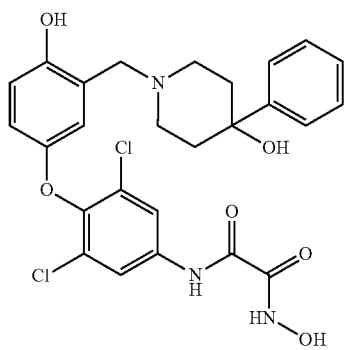 [SMILES: O=C(NO)C(=O)Nc1cc(Cl)c(Oc2ccc(O)c(CN3CCC(O)(c4ccccc4)CC3)c2)c(Cl)c1]

Spectrum Data of Product $^1$H NMR (DMSO-d) δ: 10.63 (br. s., 1H), 8.10 (s, 2H), 7.22-7.32 (m, 2H), 7.10-7.22 (m, 3H), 6.57-6.68 (m, 2H), 6.51 (dd, J=8.6, 3.0 Hz, 1H), 3.35 (br. s., 2H), 2.82 (d, J=10.7 Hz, 2H), 1.96 (t. J=11.1 Hz, 2H), 1.43-1.68 (m, 2H), 1.09-1.26 (m, 2H)

Example 13 Product Number: TMI-105961

Name

N1-(3,5-dichloro-4-(4-hydroxy-3-(isoindolin-2-methyl)phenoxy)phenyl)-N2-oxalyl hydroxylamine Structural Formula:

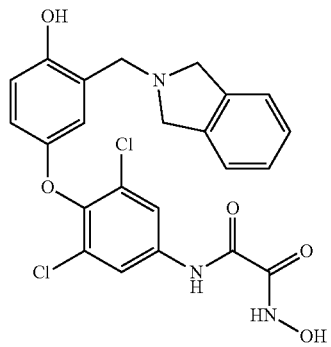 [SMILES: O=C(NO)C(=O)Nc1cc(Cl)c(Oc2ccc(O)c(CN3Cc4ccccc4C3)c2)c(Cl)c1]

Spectrum Data of Product $^1$H NMR (DMSO-d$_6$) δ: 8.09 (s, 2H), 7.07-7.36 (m, 4H), 6.64-6.82 (m, 4H), 6.56 (dd, J=8.5, 3.4 Hz, 2H), 3.79-3.91 (m, 4H), 1.33 (d, J=4.8 Hz, 2H)

Example 14 Product Number: TMI-105962

Name

N1-(3,5-dichloro-4-(3-(3,4-dihydroisoquinolin-2(1H)-methyl)-4-hydroxyphenoxy)phenyl)-N2-oxalyl hydroxylamine Structural Formula:

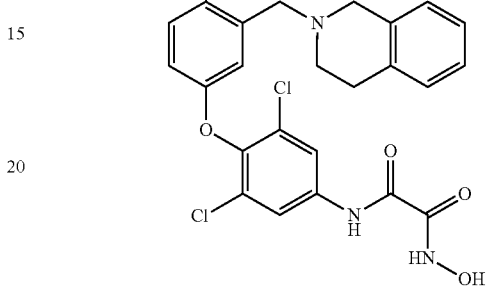

Spectrum Data of Product:
$^1$H NMR (DMSO-d$_6$) δ: 10.03 (br. s., 1H), 8.05-8.16 (m, 1H), 7.62 (s, 1H), 7.08-7.17 (m, 2H), 7.04 (d, J=5.4 Hz, 1H), 6.49-6.76 (m, 4H), 3.83 (s, 1H), 3.71 (s, 2H), 3.63 (s, 2H), 2.79 (d, J=5.6 Hz, 2H), 2.57-2.75 (m, 2H)

Example 15 Product Number TMI-105963

Name

N1-(3,5-dichloro-4-(4-hydroxy-3-((3-piperazin-1-methyl)phenoxy)phenyl)-N2-oxalyl hydroxylamine Structural Formula:

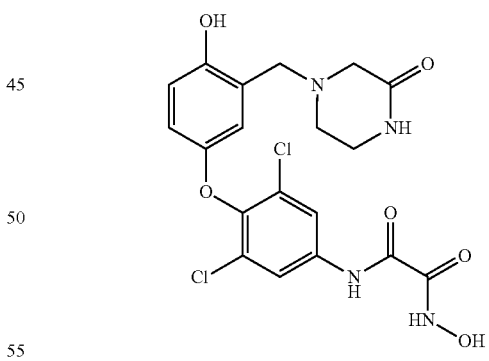

Spectrum Data of Product:
$^1$H NMR (DMSO-d$_6$) δ: 8.07-8.15 (m, 2H), 7.76 (s, 1H), 6.66-6.76 (m, 2H), 6.58 (dd, J=8.7, 3.1 Hz, 1H), 3.53 (s, 2H), 3.17 (s, 2H), 3.11 (br. s., 2H), 2.96 (s, 2H), 1.06 (t, J=7.0 Hz, 2H)

Function and Effect of Examples:

A. Mouse Experiment: TMI-105795 is Used as Test Compound in the Experiment

I. Materials and Methods

The experiment is conducted according to the procedures and details described below. To the best of our knowledge, no circumstances occurred during the course of the study that would have altered the quality and integrity of the data.

(1) Substances to be Tested

The tested compound (TMI-105795) is sub-packaged into dose volume and kept at −20° C. before use. All tested compounds (including solvents) are labeled as TDM-001-1, TDM-001-2, TDM-001-3 and TDM-001-4.

(2) Animals in Experiments

Female C3H mice (35-39 days after birth at arrival) were obtained from Beijing Vital River Laboratory Animal Technology Co., Ltd. The mice were selected for inclusion based upon acceptable clinical condition and body weight. Animals were housed randomly 5 mice per cage before grouping. All mice were kept at least one week in acclimation in the animal facility prior to any procedures. Animal identification number was labeled on the tail and cage tag respectively.

(3) Animal Feeding

Throughout the whole procedure of the experiment, the animals were housed in assigned groups (one mouse in each cage) in cages with soft bedding (corn cob or wood chips). Animals were conditioned to the same environment during the study course. Food and water were available ad libitum. Room humidity (50-70%) and temperature (21-25° C.) were maintained consistently. In addition, the study room was maintained on a 12-hour light/dark cycle.

(4) Administration of Test Compound

The test compound is TMI-105795 (solvent is polyethylene glycol/ethanol (30/70)), it is sub-packaged into dose volume and kept in −20° C. before use. It was topically administered together with solvent twice every day at 9:30 am and 4:00 pm.

(5) Experimental Design to avoid any irritation to the skin on the back of mouse. Skin color on the back was confirmed again. All mice must show pink skin, any mice that show signs of skin abrasion were excluded from the experiment. Mice were randomly divided into 5 groups and housed individually.

(2) Administration Procedures

Body weight of each mouse is recorded before administration every morning. 20 μl corresponding solution is aspirated by pipette and applied to shaving area on the back of the mouse, and then the drug solution is uniformly applied to the back between rear legs with tips, about a region with a diameter of 1 cm. It is ensured that the administered region is the same one every day, and the mouse is put into the case after drying of liquid.

(3) Scoring Procedure

All mice are scored on Monday Wednesday and Friday each week from the beginning on the Day 1 to the termination of the study, using the following scoring guidelines:

a. Hair Growth Grade (Administration Area):

0=No color change, or hair growth on the skin

1=Skin color changes uniformly over the administration area from pink to gray/black with no visible hair growth;

2=Appearance of short and sparse hair growth;

3=Full thick hair growth similar to the surrounding normal hair coat.

b. Peripheral Hair Growth (Defined as Hair Growth that is in the Dipped Area, but not in the Administration Area):

0=No color change, or hair growth on the skin;

1=Skin color changes to gray/black with no visible hair growth;

2=Peripheral sparse hair growth;

3=Peripheral thick hair growth.

| Group | Drug administration | Test compound | Number of animals | Route of Treatment | Dosing Level (μl/mouse) | Treatment Schedule |
|---|---|---|---|---|---|---|
| 1 | TDM-001-1 | Solvent PG/EtOH (30/70) | 5 | topical administration | 20 | Twice/day, 5 days/week for 3 weeks |
| re2 | TDM-001-2 | TMI-105795 (0.005%(w/v)) | 5 | topical administration | 20 | Twice/day, 5 days/week for 3 weeks |
| 3 | TDM-001-3 | TMI-105795 (0.01%(w/v)) | 5 | topical administration | 20 | Twice/day, 5 days/week for 3 weeks |
| 4 | TDM-001-4 | TMI-105795 (0.05%(w/v)) | 5 | topical administration | 20 | Twice/day, 5 days/week for 3 weeks |

(6) Behavioral Observation

Abnormal behaviors or hair growth were checked daily and data was carefully recorded during the experiment.

(7) Body Weight

During experiment, body weight of each animal was measured before administration.

(8) Scoring

Hair growth grade, peripheral hair growth, scaling, erythema will be scored on Monday, Wednesday and Friday from the beginning on the Day 1 to the termination of the experiment.

II. Reagents, Consumables and Equipment (1) Test Compound (TMI-105795)

(2) Eppendorf pipettes (3) Sterile 100 μl tips (4) Electric shaver for small animal III. Experiment Procedures (1) Grouping All experimental mice were carefully dipped with the hair on the back of the rear leg with shaver. Care must be taken c. Scaling:

0=none

1=mild

2=severe or peeling d. Erythema:

0=none

1=mild

2=severe e. Other Abnormalities (Precipitation of Test Compound at Dosing Site, Aberrant Hair Growth, Etc.)

Figure 18:
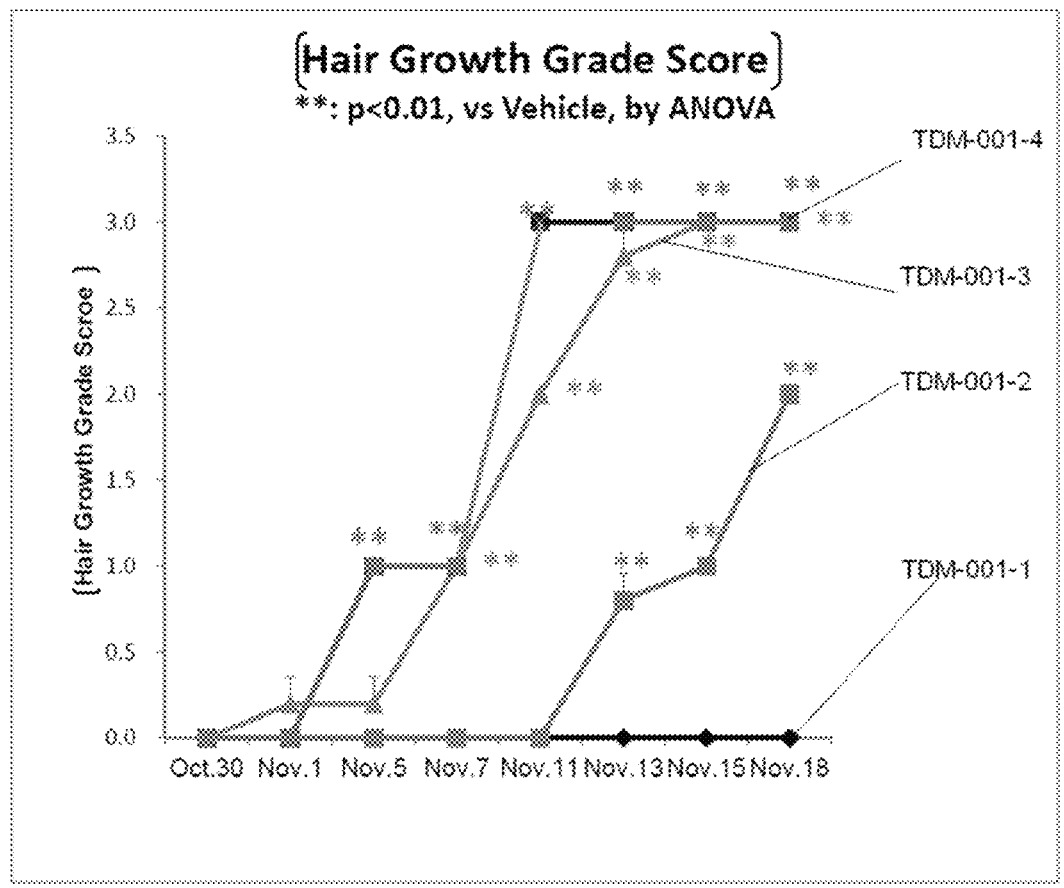

IV. Experimental Results (1) General Conditions of Mice During Experiment a. As shown in FIGS. 1(a)-(d), as compared with blank control group of solvent, the test compound (TMI-105795) shows a positive result in promoting hair growth after 3 weeks administration of test formulation at every dosing amount. There was no obvious hair growth in the solvent treatment group.

b. As shown in FIGS. 1(a)-(d), dose dependent effect is observed for different dose of the test compound obviously. Higher dose of test compound shows better effect in promoting hair growth compared with that of lower dose. As shown in FIG. 18, according to the scoring results of different mice in the experiment, no hair growth was observed for the blank control group of solvent, obvious difference was observed for the TDM-001-2 group (0.005% (w/v) compared with TDM-001-3 (i.e., 0.01% (w/v)) and TDM-001-4 (i.e., 0.05% (w/v)) groups.

Obvious difference of hair growth rate was observed for the groups with different doses of test compound. Hair growth rate in TDM-001-2 group is far slower than the grow rate in TDM-001-3 and TDM-001-4.

Specifically, for the mice in TDM-001-2 administration group, the skin became black on the day 12 of topical administration and hair growth was observed on the day 16. Continuous hair growth was observed on the following days.

For the mice in TDM-001-3 administration group, the skin became black on day 2 of topical administration and hair growth was observed on the day 6. Continuous hair growth was observed on the following days.

For the mice in TDM-001-4 topical administration group, the skin became black on day 2 of topical administration and hair growth was observed on the day 8. Continuous hair growth was observed on the following days.

Figure 17:
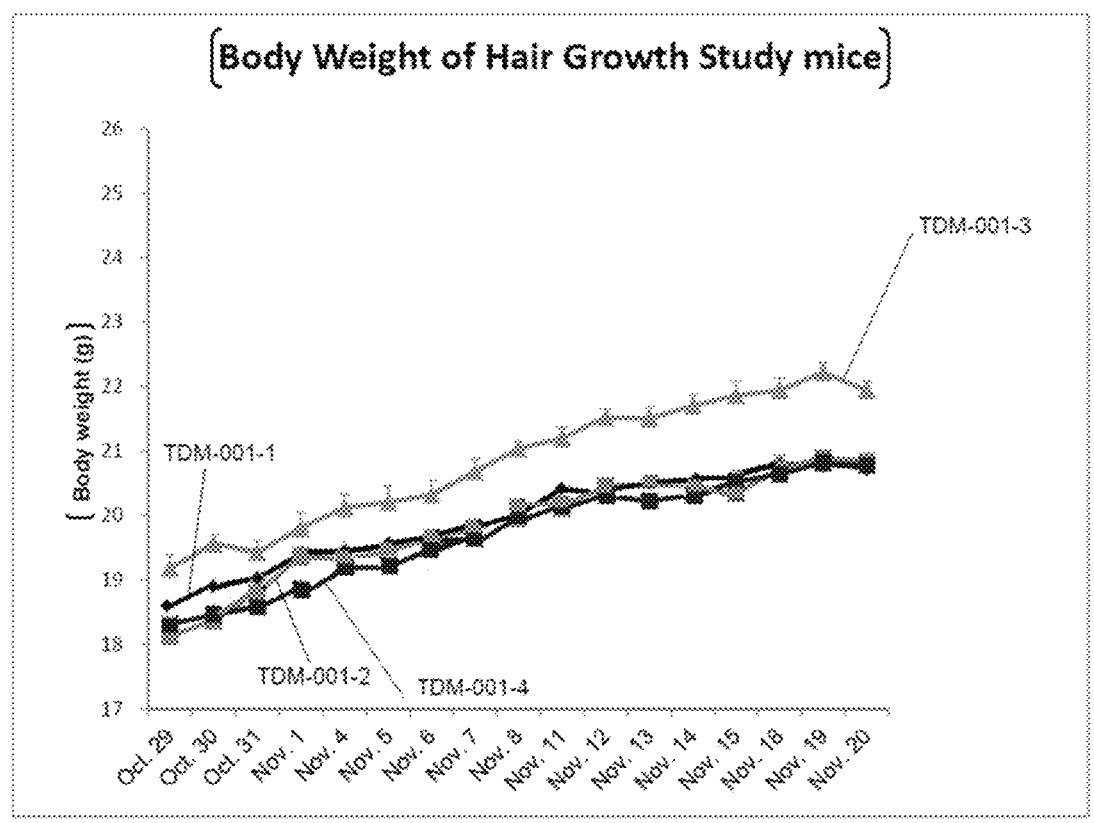
FIG. 17. Diagram of body weight changes of mice during administration
FIG. 18. Diagram of scoring on hair growth during administration
FIG. 19. Diagram of scoring on scaling during administration.
Figure 19:
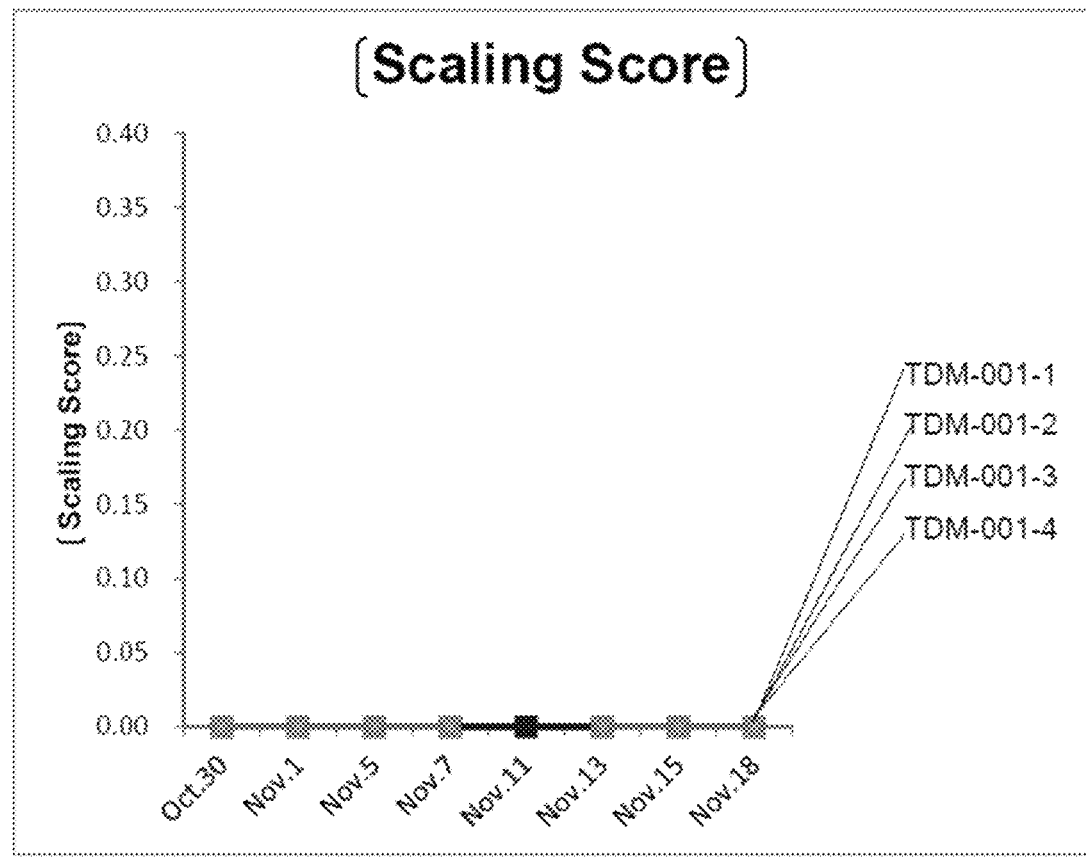
Figure 20:
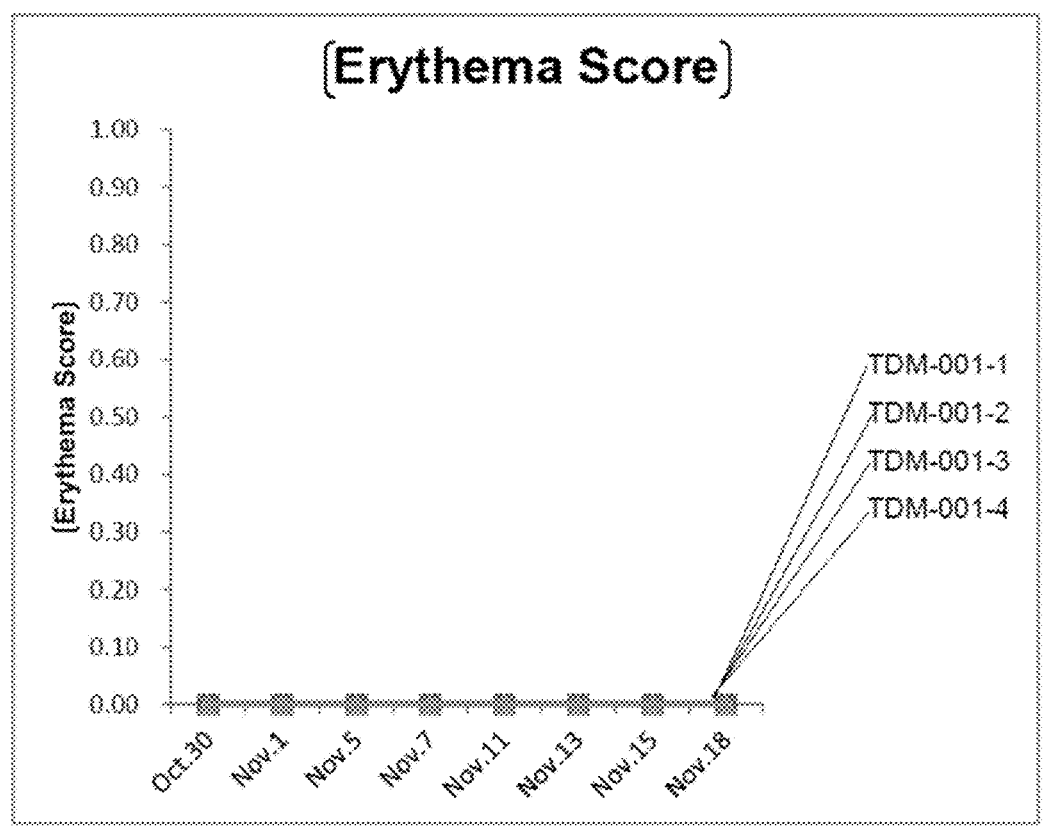
FIG. 20. Diagram of scoring on erythema during administration.

It can be seen from the experiment that, the onset of new hair growth and hair growth rate of mice in the low dose group are dearly delayed as compared to the high dose group. Although difference exists in hair growth progression with various doses, when the test compound dose reaches 0.01%, no obvious difference was observed in hair growth once the full coat hair grows to a certain level.

c. As shown in FIG. 17, the body weight of all mice in each group increased slowly, indicating the test compound would not induce the loss of animal body weight.

d. As shown in FIGS. 19 and 20, no significant findings were observed with scorings of scaling and erythema of the mice skin in all treatment groups.

(2) Summary of Evaluation Results a. Positive result of promoting hair growth was observed for the test compound even at the lowest dosage in the experiment.

b. Scaling and erythema were not observed in all treatment groups for all mice.
Except the above observations, all mice showed normal skin color and no abnormal symptoms.

V. Conclusion for Examples

The test compound TMI-105795 significantly promotes the hair growth in C3H mice.

C3H mouse's dorsal hair is known to have a time-synchronized hair growth cycle. From about 2.5 to 3.5 weeks old and 5 to 14 weeks old, the dorsal hairs are in the telogen phase (resting phase). From 0 to 2.0 weeks old and 4.0 to 4.5 weeks old, the dorsal hairs are in the anagen phase.

In the experiment, the effect of the test compound (TMI-105795) on hair growth in C3H mice was tested. All doses of test compound (TMI-105795) showed positive results in promoting hair growth, when compared with solvent group, after 3 weeks topical administration of test formulation. At the same time, dose-dependent hair growth effect was clearly observed and related to the three different doses of the test compound.

Therefore, this study showed the test compound (TMI-105795) could change hair growth cycle and promote hair growth.

It is worth pointing out here, that the compounds in the other examples show similar effect. Redundant description is skipped here.

B: Thyroid Receptor TRβ Agonist Assay

I. Detailed experimental methods

1. Plating Cells (1) Two hours before cell seeding, pre-coat 96-well plates are added with 40 µl poly-D-lysine, incubated at room temperature.

(2) The residual poly-D-lysine is removed. On the 96-well plate, HEK-293 cells are plated at a density of $4.0 \times 10^4$ cells/well in DMEM medium containing 10% FBS. The cells are cultured at 37° C. overnight.

2. Co-Transfection (1) The culture medium is removed 2 hours before transfection. 100 µl of DMEM culture medium containing 10% FBS treated by activated carbon is added to each well, and incubated at 37° C. for 2 hours.

(2) Preparation of plasmid DNA-XtremeGENE HP liposome complex.

1. Transfection reagent X-tremeGENE HP is warmed to room temperature and vortexed gently before use.

2. Opti-MEM I Reduced-Serum culture Medium is added in a sterile tube.

3. For each reaction system, 50 ng thyroid receptor (TRβ) plasmid DNA and 50 ng luciferase reporter gene plasmid DNA of thyroid hormone response element are added. Mixing it completely by gentle pipeting.

4. 0.2 µl of transfection reagent X-tremeGENE HP is added to the diluted co-transfected DNA mixture. Mixing it completely by gentle pipeting.

5. The mixture is incubated at room temperature for 20 minutes to form plasmid DNA-XtremeGENE HP liposome complex.

(3) 10 µl of the complex is added to each well in a 96 well plate. Gently shaking the culturing plate to evenly distribute the complex.

(4) The culture is incubated at 37° C. for 24 hours.

3. Agonist Compound Treatment:

(1) Preparation of compound diluent: for each compound, half-log dilutions of each test compound is prepared using DMEM medium containing 10% charcoal stripped FBS (containing 0.1% DMSO), with a maximum concentration of 10 µM of the test compound.

(2) Removing the culture medium and adding the formulated compound diluent (the final DMSO concentration is 0.1%).

(3) For blank control, DMEM medium containing 10% charcoal stripped FBS (containing 0.1% DMSO) is added.

(4) Incubating at 37° C. for 24 hours.

4. Luciferase Reporter Gene Assay:

(1) Removing the culture medium, adding 40 µl phosphate (PBS) buffer to each well.

(2) Adding 40 µl Bright-Glo reagent to each well and vortexing for 30 seconds, followed by incubation in dark for 2 min.

(3) Transferring 70 µl cell lysate from each well into a white polystyrene 96-well plate.

(4) Detecting the Luciferase signal intensity by Envision.

II. Experimental Results (as shown in FIGS. 2-7)

| Compound Number | EC50 (nM) |
| --- | --- |
| 105798 | 179.4 |
| TMI-105902 | 250.3 |
| TMI-105903 | 136.4 |

-continued

| Compound Number | EC50 (nM) |
|---|---|
| TMI-105905 | 399.5 |
| TMI-105965 | 95.97 |
| TMI-105966 | 61.13 |
| TMI-105906 | 925.4 |
| TMI-105956 | 6521 |
| TMI-105957 | 8757 |
| TMI-105958 | 9701 |
| TMI-105959 | 617.2 |
| TMI-105960 | 6.478E7 |
| TMI-105961 | 9243 |
| TMI-105962 | 3719 |
| TMI-105963 | 9577 |

We claim:

1. A small molecule compound, characterized in that, it is represented by the following structural formula:

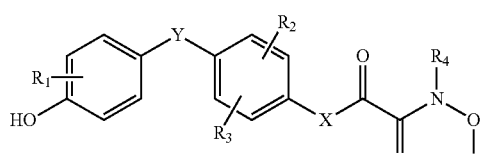

$R_1$ is selected from hydrogen, halogen, $C_1$-$C_6$alkyl or optionally substituted with 1-3 substituents, cyano, isocyanate, amide, iso-sulfonamide ($SO_2NHR$), iso-sulfinyl (SONH), sulfonamide ($NHSO_2R$), sulfonamido (NHSOR), S-alkyl, S-aryl, S-heteroaryl (SHet);

wherein the substituents are selected from halogen, aryl, substituted aryl, heteroaryl, O-alkyl, O-aryl, O-heteroaryl, N-alkyl, N-aryl, N-heteroaryl;

$R_2$ is selected from Hydrogen, halogen, $C_1$-$C_6$ alkyl or substituted alkyl, alkoxy, aryl, substituted aryl, benzyl, substituted benzyl;

$R_3$ is selected from Hydrogen, halogen, $C_1$-$C_6$ alkyl or substituted alkyl, alkoxy, aryl, substituted aryl, benzyl, substituted benzyl;

$R_4$ is selected from hydrogen, $C_1$-$C_6$ alkyl or substituted alkyl;

$R_5$ is selected from hydrogen, $C_1$-$C_6$ alkyl or substituted alkyl;

X is selected from alkylene or substituted alkylene, amino or substituted amino;

Y is selected from alkylene or substituted alkylene, oxygen, sulfur, amino, carbonyl, sulfoxide, sulfone.

2. The small molecule compound of claim 1, characterized in that, it is represented by the following structural formula:

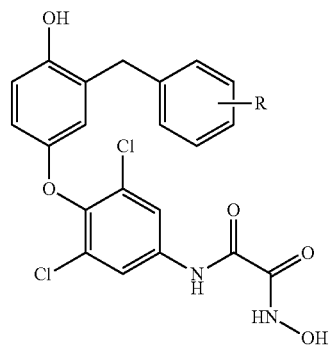

wherein R is halogen, hydroxyl, hydrogen, or mono- or polysubstituted alkylsulphonyl, alkyl, methoxy, nitro, amino, carboxyl, ester, aryl, or benzyl.

3. The small molecule compound of claim 1, characterized in that, it is represented by the following structural formula:

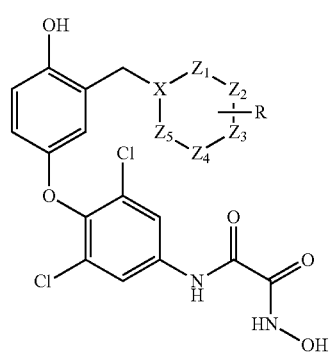

wherein R is halogen, hydroxyl, hydrogen, or mono- or polysubstituted alkylsulphonyl, alkyl, methoxy, nitro, amino, carboxyl, ester, aryl, benzyl, O-alkyl, O-aryl, O-heteroaryl, N-alkyl, N-aryl, or N-heteroaryl;

X is —CH— or nitrogen;

$Z_1$, $Z_2$, $Z_3$, $Z_4$, $Z_5$ are carbon, oxygen, sulfur, nitrogen, carbonyl; and X, $Z_1$, $Z_2$, $Z_3$, $Z_4$ and $Z_5$ form aromatic or nonaromatic lactam.

4. The small molecule compound of claim 1, characterized in that, it is represented by the following structural formula:

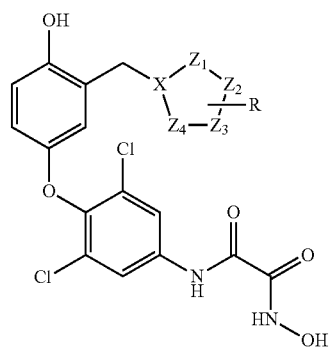

wherein R is halogen, hydroxyl, hydrogen, mono- or polysubstituted alkylsulphonyl, alkyl, methoxy, nitro, amino, carboxyl, ester, aryl, benzyl, O-alkyl, O-aryl, O-heteroaryl, N-alkyl, N-aryl, N-heteroaryl;

X is —CH— or nitrogen;

$Z_1$, $Z_2$, $Z_3$, $Z_4$ are carbon, oxygen, sulfur, nitrogen, carbonyl, and

X, $Z_1$, $Z_2$, $Z_3$, and $Z_4$ form aromatic or nonaromatic lactam.

5. The small molecule compound of claim 1, characterized in that, it is

N1-(3,5-dichloro-4-(3-(4-fluorobenzyl)-4-hydroxyphenoxy)phenyl)-N2-oxalyl hydroxylamine; or N1-(3,5-dichloro-4-(3-(4-methylsulfonylbenzyl)-4-hydroxyphenoxy)phenyl)-N2-oxalyl hydroxylamine; or N1-(3,5-dichloro-4-(3-(4-methylbenzyl)-4-hydroxyphenoxy)phenyl)-N2-oxalyl hydroxylamine; or N1-(3,5-dichloro-4-(3-(3, 4-dichlorobenzyl)-4-hydroxyphenoxy)phenyl)-N2-oxalyl hydroxylamine; or N1-(3,5-dichloro-4-(3-(3-fluorobenzyl)-4-hydroxyphenoxy)phenyl)-N2-oxalyl hydroxylamine; or N1-(3,5-dichloro-4-(3-(2-fluorobenzyl)-4-hydroxyphenoxy)phenyl)-N2-oxalyl hydroxylamine; or N1-(3,5-dichloro-4-4-hydroxy-3-(morpholinomethyl) phenoxy)phenyl)-N2-oxalyl hydroxylamine; or N1-(3,5-dichloro-4-(4-hydroxy-3-(4-hydroxypiperidin-1-yl)phenoxy)phenyl)-N2-oxalyl hydroxylamine; or N1-(3,5-dichloro-4-(4-hydroxy-3-(4-methylpiperazin-1-yl)phenoxy)phenyl)-N2-oxalyl hydroxylamine; or N1-(3,5-dichloro-4-(4-hydroxy-3-(4-methylpiperazin-1-methyl)phenoxy)phenyl)-N2-oxalyl hydroxylamine; or N1-(3,5-dichloro-4-(4-hydroxy-3-(pyrrolidin-1-methyl) phenoxy)phenyl)-N2-oxalyl hydroxylamine; or N1-(4-(3-((4-benzylpiperidin-1-methyl)-4-hydroxyphenoxy)-3,5-dichlorophenyl)-N2-oxalyl hydroxylamine; or N1-(3,5-dichloro-4-(4-hydroxy-3-((4-hydroxy-4-phenylpiperidin-1-methyl)phenoxy)phenyl)-N2-oxalyl hydroxylamine; or N1-(3,5-dichloro-4-(4-hydroxy-3-(isoindolin-2-methyl) phenoxy)phenyl)-N2-oxalyl hydroxylamine; or N1-(3,5-dichloro-4-(3-(3,4-dihydroisoquinolin-2(H)-methyl)-4-hydroxyphenoxy)phenyl)-N2-oxalyl hydroxylamine; or N1-(3,5-dichloro-4-(4-hydroxy-3-(3-piperazinone-1-methyl)phenoxy)phenyl)-N2-oxalyl hydroxylamine.

6. A process for synthesizing a small molecule compound, characterized in that:

step 1: 4-methoxyphenol is reacted with 1,2,3-trichloro-5-nitrobenzene to form 1,3-dichloro-2-(4-methoxyphenoxy)-5-nitrobenzene;

step 2: 1,3-dichloro-2-(4-methoxyphenoxy)-5-nitrobenzene is reacted with benzoic acid derivatives to form (5-(2,6-dichloro-4-nitrophenoxy)-2-methoxyphenyl) (substituted phenyl) methyl ketone);

step 3: 1,3-dichloro-2-(3-(substituted benzyl)-4-methoxyphenoxy)-5-nitrobenzene is obtained from reduction of carbonyl of (5-(2,6-dichloro-4-nitrophenoxy)-2-methoxyphenyl)(substituted phenyl) methyl ketone to methylene;

step 4: 3,5-dichloro-4-(3-(substituted benzyl)-4-methoxyphenoxy)-aniline is obtained from reduction of nitro of 1,3-dichloro-2-(3-(substituted benzyl)-4-methoxyphenoxy)-5-nitrobenzene to amino;

Step 5: 3,5-dichloro-4-(3-(substituted benzyl)-4-methoxyphenoxy)-aniline is reacted with ethyl oxaloyl monochloride to form 2-((3,5-dichloro-4-(3-(substituted benzyl)-4-methoxyphenoxy)phenyl)amino)-oxoacetate;

Step 6: 2-((3,5-dichloro-4-(3-(substituted benzyl)-4-methoxyphenoxy) phenyl)amino)-oxoacetate is reacted with hydroxylamine hydrochloride to form N1-(3,5-dichloro-4-(3-(substituted benzyl)-4-methoxyphenoxy) phenyl)-N2-oxalyl hydroxylamine;

Step 7: after demethylation of methoxyl of N1-(3,5-dichloro-4-(3-(substituted benzyl)-4-methoxyphenoxy) phenyl)-N2-oxalyl hydroxylamine, a target small molecule compound can be obtained.

7. The process for synthesizing a small molecule compound of claim 6, characterized in that: the derivatives of benzoic acid can be replaced with the compound having the following structure:

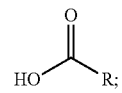

wherein R can be $C_1$-$C_6$ alkyl or optionally substituted with 1-3 substituents;

the substituents are selected from halogen, aryl, substituted aryl, heteroaryl, O-alkyl, O-aryl, O-heteroaryl, N-alkyl, N-aryl, N-heteroaryl, S-alkyl, S-aryl and S-heteroaryl.

8. The process for synthesizing a small molecule compound of claim 6, characterized in that:

in step 1, the molar ratio of 4-methoxyphenol to 1,2,3-trichloro-5-nitrobenzene is 1:1-2;

in step 2, the molar ratio of 1,3-dichloro-2-(4-methoxyphenoxy)-5-nitrobenzene to benzoic acid derivative is 1:1.25-2;

in step 4, the molar ratio of 1,3-dichloro-2-(3-(substituted benzyl)-4-methoxyphenoxy)-5-nitrobenzene to reducing agent is 1:10-20;

in step 5, the molar ratio of 3,5-dichloro-4-(3-(substituted benzyl)-4-methoxyphenoxy)aniline to ethyl oxalyl monochloride is 1:1.5-3;

in step 6, the molar ratio of 2-((3,5-dichloro-4-(3-(substituted benzyl)-4-methoxyphenoxy)phenyl)amino)-oxoacetate to hydroxylamine hydrochloride is 1:5-10.

9. The process for synthesizing a small molecule compound of claim 6, characterized in that: in step 1, the reaction is carried out under strong basic condition, the strong bases can be selected from $KNH_2$, $NaNH_2$, NaCN, KCN, butyl lithium, lithium diisopropylamine, benzyl lithium, Grignard reagents, lithium alkylcuprate, sodium methoxide, sodium ethoxide, potassium ethoxide, NaOtBu, NaOH or KOH, and the reaction temperature is 120-160° C.;

in step 2, reaction is carried out in Eaton's Reagent, the reaction temperature is 80-130° C.

10. The process for synthesizing a small molecule compound of claim 6, characterized in that: in step 3, trifluoroacetic acid and triethyl silane are used to reduce the carbonyl group to methylene group, wherein the molar ratio of the reactants (5-(2,6-dichloro-4-nitrophenoxy)-2-methoxyphenyl)(substituted phenyl) methyl ketone:trifluoroacetic acid: triethyl silane 1:4-6:3-5.

11. The process for synthesizing a small molecule compound of claim 6, characterized in that: demethylation of step 7 can be carried out using aluminum trichloride (AlCl3), zinc chloride (ZnCl2) or boron tribromide (BBr3).

* * * * *